(12) United States Patent
Ormerod et al.

(10) Patent No.: US 9,586,893 B2
(45) Date of Patent: Mar. 7, 2017

(54) PROCESSES AND INTERMEDIATES FOR PREPARING A MACROCYCLIC PROTEASE INHIBITOR OF HCV

(75) Inventors: Dominic John Ormerod, Hoogstraten (BE); Dominique Paul Michel Depre, Hamme-Mille (BE); Andras Horvath, Turnhout (BE)

(73) Assignee: Janssen Pharmaceuticals, Titusville, NJ (US)

( * ) Notice: Subject to any disclaimer, the term of this patent is extended or adjusted under 35 U.S.C. 154(b) by 159 days.

(21) Appl. No.: 13/634,996

(22) PCT Filed: Mar. 16, 2011

(86) PCT No.: PCT/EP2011/053957
§ 371 (c)(1),
(2), (4) Date: Sep. 14, 2012

(87) PCT Pub. No.: WO2011/113859
PCT Pub. Date: Sep. 22, 2011

(65) Prior Publication Data
US 2013/0005976 A1    Jan. 3, 2013

(30) Foreign Application Priority Data
Mar. 16, 2010 (EP) ..................................... 10156681

(51) Int. Cl.
| | |
|---|---|
| C07D 493/08 | (2006.01) |
| C07C 255/57 | (2006.01) |
| C07C 51/02 | (2006.01) |
| C07C 51/41 | (2006.01) |
| C07C 51/43 | (2006.01) |
| C07C 67/03 | (2006.01) |
| C07C 67/31 | (2006.01) |
| C07C 69/757 | (2006.01) |
| C07C 205/57 | (2006.01) |
| C07C 215/30 | (2006.01) |
| C07C 231/12 | (2006.01) |
| C07C 235/40 | (2006.01) |
| C07C 317/44 | (2006.01) |
| C07D 251/28 | (2006.01) |
| C07D 251/30 | (2006.01) |
| C07D 309/30 | (2006.01) |
| C07D 417/04 | (2006.01) |
| C07D 417/14 | (2006.01) |
| C07D 491/18 | (2006.01) |
| C07C 201/12 | (2006.01) |

(52) U.S. Cl.
CPC ............ *C07C 255/57* (2013.01); *C07C 51/02* (2013.01); *C07C 51/412* (2013.01); *C07C 51/43* (2013.01); *C07C 67/03* (2013.01); *C07C 67/31* (2013.01); *C07C 69/757* (2013.01); *C07C 201/12* (2013.01); *C07C 205/57* (2013.01); *C07C 215/30* (2013.01); *C07C 231/12* (2013.01); *C07C 235/40* (2013.01); *C07C 317/44* (2013.01); *C07D 251/28* (2013.01); *C07D 251/30* (2013.01); *C07D 309/30* (2013.01); *C07D 417/04* (2013.01); *C07D 417/14* (2013.01); *C07D 491/18* (2013.01); *C07B 2200/07* (2013.01); *C07C 2101/08* (2013.01)

(58) Field of Classification Search
CPC ..................................................... C07D 493/08
See application file for complete search history.

(56) References Cited

U.S. PATENT DOCUMENTS

| | | | |
|---|---|---|---|
| 2003/0181753 A1* | 9/2003 | Groger .................... | C07C 67/08 560/1 |
| 2007/0185346 A1* | 8/2007 | Vaidya ......................... | 562/401 |

FOREIGN PATENT DOCUMENTS

| | | |
|---|---|---|
| EP | 0118934 A | 9/1984 |
| JP | 59148749 A | 8/1984 |
| JP | 6124539 A | 2/1986 |
| JP | 08231469 A | 9/1996 |
| WO | 2005073195 A2 | 8/2005 |
| WO | 2005073216 A2 | 8/2005 |
| WO | 2007014926 A1 | 2/2007 |
| WO | 2008092955 A1 | 8/2008 |

OTHER PUBLICATIONS

Bartlett, Paul A. "Total synthesis of brefeldin A." Journal of the American Chemical Society, 1978, 100(15), 4858-65.*
"ChiroSolv Resolving Kits" ChemFiles Supplement I 2008.*
Garrett "New observations on peptide bond formation using CDMT" Tetrahedron Letters 2002 43 4161-4165.*
Rohm and Haas, "The Sodium Borohydride Digest" Oct. 2003, pp. 1-2, 7-11.*
Kozma, David "CRC Handbook of Optical Resolutions Via Diastereomeric Salt Formation" 2002 CRC Press: Washington, DC, Chapters 4, 5 and 6.*

(Continued)

*Primary Examiner* — David K O'Dell
(74) *Attorney, Agent, or Firm* — Andrea Jo Kamage

(57) ABSTRACT

A process for preparing [(1R,2R)-4-oxo-1,2-cyclopentanedicarboxylic acid II, by the resolution of racemic 4-oxo-1,2-cyclopentanedicarboxylic acid (V), said process comprising:
(a) reacting 4-oxo-1,2-cyclopentanedicarboxylic acid (V) with brucine or (1R,2S)-(−)-ephedrine, thus preparing the bis-brucine or bis-(1R,2S)-(−)-ephedrine salt of (V), and
(b) precipitating selectively the bis-brucine or bis-(1R,2S)-(−)-ephedrine salt of (1R,2R)-4-oxo-1,2-cyclopentanedicarboxylic acid II, while the bis-brucine or bis-(1R,2S)-(−)-ephedrine salt of [(1S,2S)-4-oxo-1,2-cyclopentanedicarboxylic acid stays in solution;
(c) liberating the acid II by removal of brucine or (1R,2S)-(−)-ephedrine from the precipitated salt obtained in step (b).

2 Claims, No Drawings

(56) References Cited

OTHER PUBLICATIONS

Kaminska "2-Acyloxy-4,6-dimethoxy-1,3,5-triazine—A New Reagent for Ester Synthesis" Synthesis 1999, 4, 593-596.*
Goldsworthy "Resolution of trans-cycloPentane-1 : 2-dicarboxylic Acid" 1914 J. Chem. Soc. 105, 2639.*
Clarke "Combining pot, atom and step economy (PASE) in organic synthesis. Synthesis of tetrahydropyran-4-ones." Green Chemistry 2007, 9(5) 438-440.*
Ahlbrecht, et al., Optical Resolution by Cristallization of Diastereomers, Methoden der organischen Chemie, May 24, 1995, 81-94,99-101 (XP-002594193), vol.E21a.
Esus Ezquerra et al, Conformationally Constrained ACPD Analogues. Synthesis and Resolution of 3-Aminobicyclo[3,3,0]Octane-1,3-Dicarboxylic Acids, Tetrahedron, 1995, p. 3271-3278, vol. 51, No. 11.
Johansson, et al., Potent inhibitors of the hepatitis C virus NS3 protease: Use of a novel P2 cyclopentane-derived template, Bioorganic & Medicinal Chemistry, Aug. 1, 2006, pp. 5136-5151—XP025133411, vol. 14 No. 15.
Velusamy, et al., Copper(ii)-Catalyzed Oxidation of Alcohols to Carbonyl Compounds with Hydrogen Peroxide, Eur. J. Org. Chem., 2003, pp. 3913-3915, DOI: 10.1002/ejoc.200300324, Wiley-VCH Verlag GmbH & Col.
Honda et al., "A Synthesis of (+)—Brefeldin A" Tetrahedron letters, vol. 22, No. 28, pp. 2679-2682 (1981).
Raboisson et al., "Structure-activity relationship study on a novel series of cyclopentane-containing macrycyclic inhibitors of the hepatitis C virus NS3/4A protease leading to the discovery of TMC435350", Bioorganic & Medicinal Chemistry Letters, 18, pp. 4853-4858 (2008).

\* cited by examiner

PROCESSES AND INTERMEDIATES FOR PREPARING A MACROCYCLIC PROTEASE INHIBITOR OF HCV

This application is a national stage application of PCT/EP2011/053957, filed Mar. 16, 2011, which claims priority benefit of Application No. EP 10156681.8 filed Mar. 16, 2010. The complete disclosures of the aforementioned related patent applications are hereby incorporated herein by reference for all purposes.

FIELD OF THE INVENTION

The present invention relates to synthesis procedures and synthesis intermediates of a macrocyclic protease inhibitor of the hepatitis C virus (HCV).

BACKGROUND OF THE INVENTION

The Hepatitis C Virus (HCV) is the leading cause of chronic hepatitis, which can progress to liver fibrosis leading to cirrhosis, end-stage liver disease, and HCC (hepatocellular carcinoma), making it the leading cause of liver transplantations. Current anti-HCV therapy, based on (pegylated) interferon-alpha (IFN-α) in combination with ribavirin, suffers from limited efficacy, significant side effects, and is poorly tolerated in many patients. This prompted the search for more effective, convenient and better-tolerated therapy.

Replication of the genome of HCV is mediated by a number of enzymes, amongst which is HCV NS3 serine protease and its associated cofactor, NS4A. Various agents that inhibit this enzyme have been described. WO 05/073195 discloses linear and macrocyclic NS3 serine protease inhibitors with a central substituted proline moiety and WO 05/073216 with a central cyclopentane moiety. Amongst these, the macrocyclic derivatives are attractive by their pronounced activity against HCV and attractive pharmacokinetic profile.

WO 2007/014926 describes macrocyclic cyclopentane and proline derivatives including the compound of formula I, with the structure represented hereafter. The compound of formula I is a very effective inhibitor of the HCV serine protease and is particularly attractive in terms of pharmacokinetics. Due to its favourable properties it has been selected as a potential candidate for development as an anti-HCV drug. Consequently there is a need for producing larger quantities of this active ingredient based on processes that provide the product in high yield and with a high degree of purity. WO 2008/092955 describes processes and intermediates to prepare the compound of formula I.

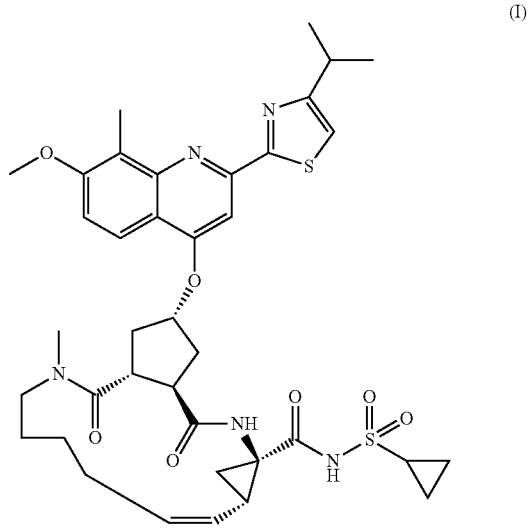 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1C]

(I)

According to WO 2007/014926 the compound of formula I can be prepared starting from the bicyclic lactone carboxylic acid referred to as compound 39 in example 4, or in the general description of this reference as compound 17b, or as compound VII in this description and claims. The carboxylic acid in bicyclic lactone carboxylic acid is coupled with N-methylhex-5-enylamine 38, followed by lactone opening to 4-hydroxycyclopentane derivative 41. The latter derivative 41 is then coupled with aminocyclo-propylcarboxylic ester to cyclopentane dicarboxylic acid diamide 43, which is coupled with quinoline 36 in an Mitsunobu ether-forming reaction, which involves an inversion at the hydroxy-bearing carbon. The resulting intermediate 44 is cyclized via a metathesis reaction to a macrocyclic derivative, in which the ester group is hydrolysed and coupled with cyclopropylsulfonylamide to yield the desired end product of formula I. These reactions are illustrated in the following scheme in which R represents $C_{1-4}$alkyl and in example 4, R is ethyl.

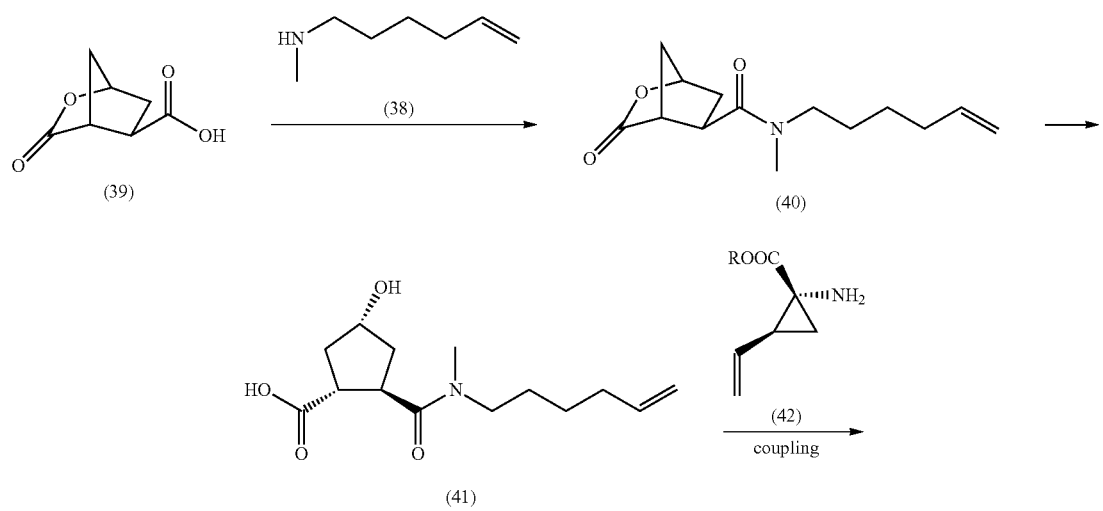

-continued
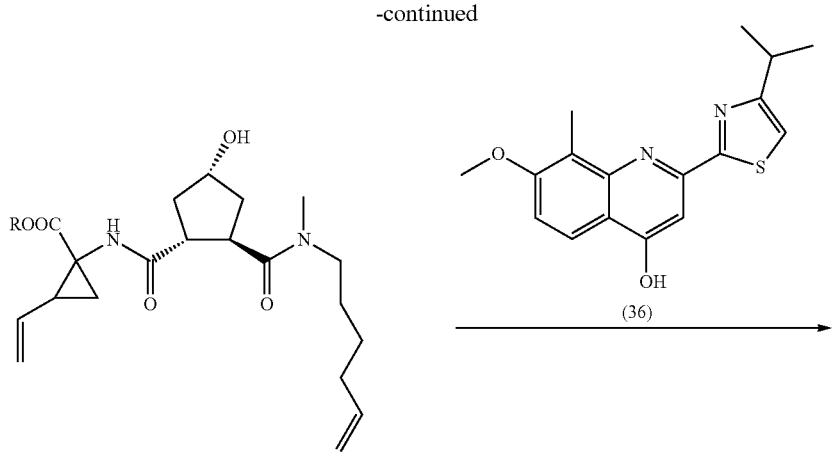
(43)
(36)
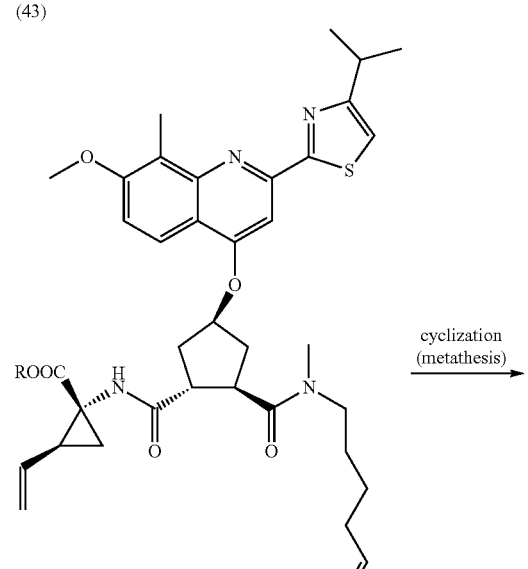
cyclization (metathesis)
(44)
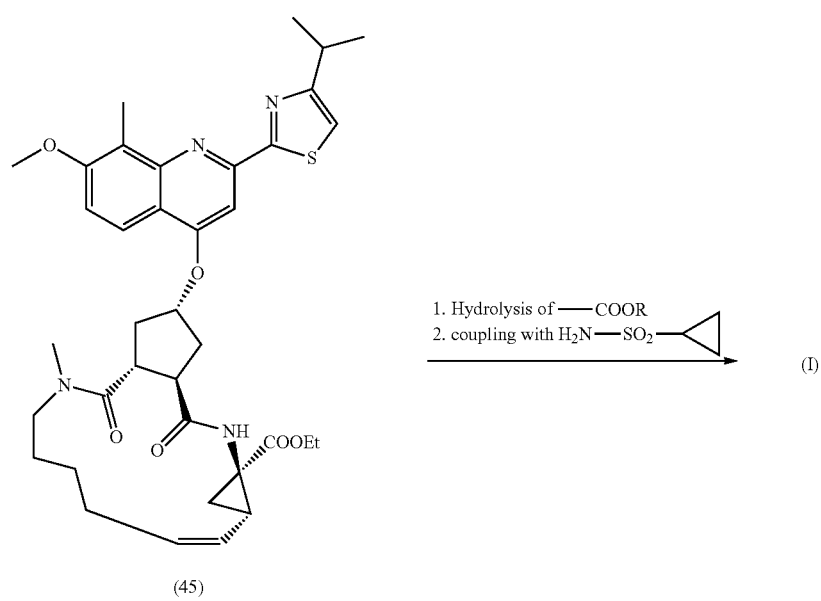
(45)
1. Hydrolysis of —COOR
2. coupling with $H_2N-SO_2-$ ◁
(I)

The enantiomerically pure bicyclic lactone 39 was prepared starting from an enantiomer of 3,4-bis(methoxycarbonyl)cyclo-pentanone, referred to as (17a) in WO 2007/014926. The latter was prepared as described by Rosenquist et al. in Acta Chemica Scandinavica 46 (1992) 1127-1129. Racemic cyclohexene dicarboxylic acid methyl ester was synthesized via a Diels-Alder reaction of 3-sulfolene and dimethyl fumarate, followed by oxidative cleavage of the double bond, cyclization, and decarboxylation, resulting in (+) 4-ketocyclopentane dicarboxylic acid dimethyl ester. Resolution of the latter by hydrolysis using pig liver esterase resulted in the corresponding (+)-monoacid and the (−) diester, which is intermediate (17a) of WO 2007/014926.

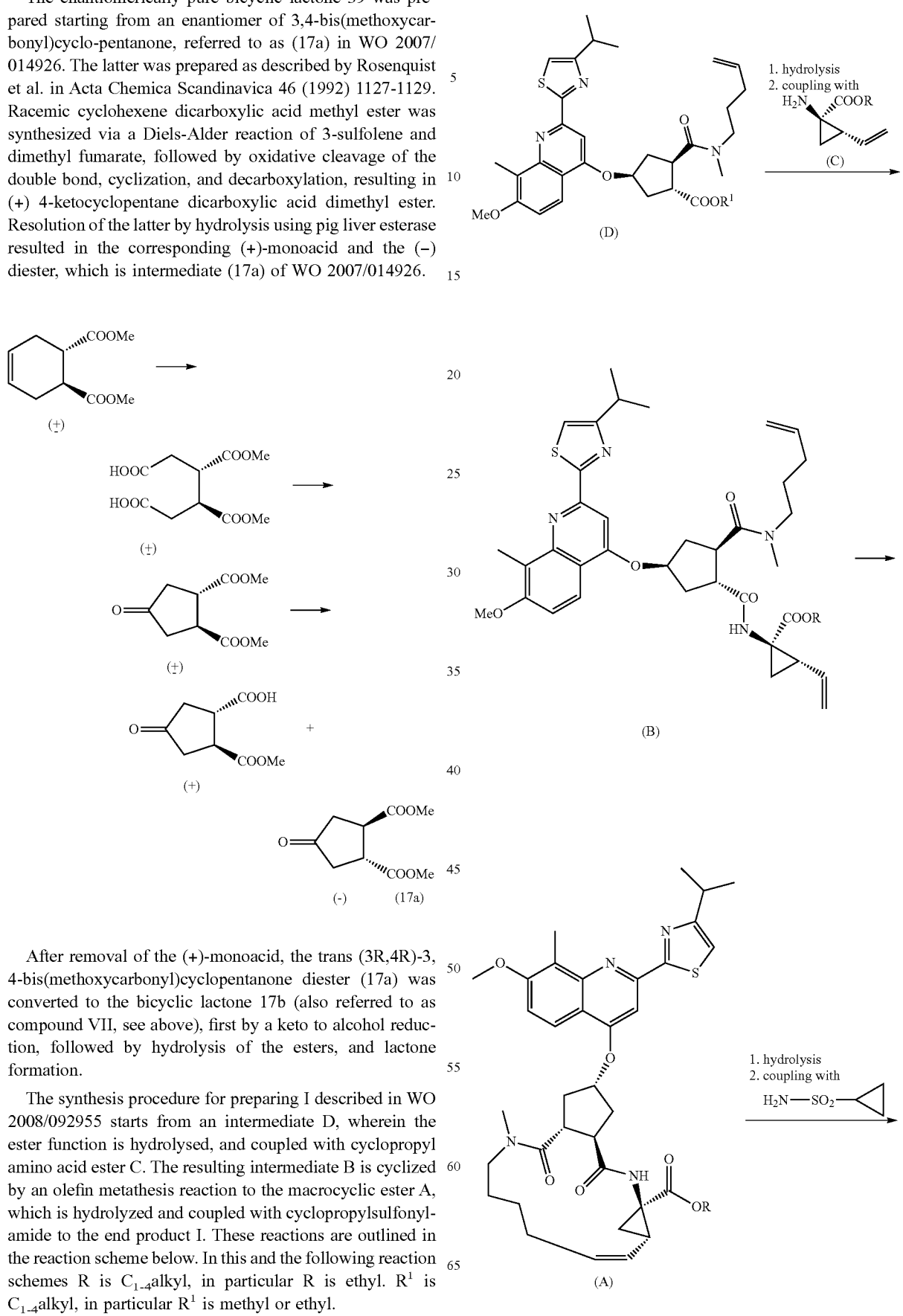

After removal of the (+)-monoacid, the trans (3R,4R)-3,4-bis(methoxycarbonyl)cyclopentanone diester (17a) was converted to the bicyclic lactone 17b (also referred to as compound VII, see above), first by a keto to alcohol reduction, followed by hydrolysis of the esters, and lactone formation.

The synthesis procedure for preparing I described in WO 2008/092955 starts from an intermediate D, wherein the ester function is hydrolysed, and coupled with cyclopropyl amino acid ester C. The resulting intermediate B is cyclized by an olefin metathesis reaction to the macrocyclic ester A, which is hydrolyzed and coupled with cyclopropylsulfonylamide to the end product I. These reactions are outlined in the reaction scheme below. In this and the following reaction schemes R is $C_{1-4}$alkyl, in particular R is ethyl. $R^1$ is $C_{1-4}$alkyl, in particular $R^1$ is methyl or ethyl.

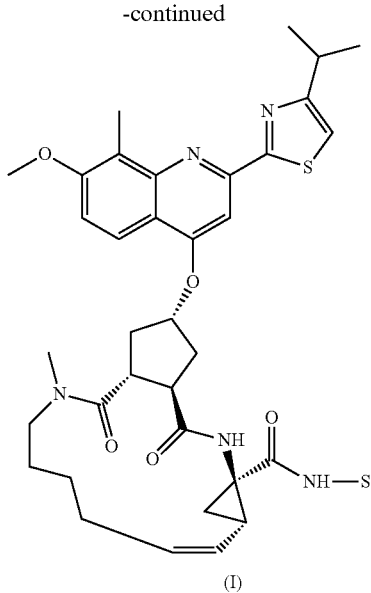

Intermediate D in turn can be prepared starting from a hydroxycyclopentyl bis-ester of formula H1, by either (a) reacting H1 with a thiazolyl substituted quinolinol E to the quinolinyloxy-cyclopentyl bis-ester of formula K, followed by a cleavage of the benzyl ester group to the mono-carboxylic acid J, which in turn is coupled with an N-methyl hexenamine to intermediate D; or (b) cleaving the benzyl ester in H1 to the mono-carboxylic acid G, coupling the latter with an N-methyl hexenamine to the hydroxycyclopentylamide F, which in turn is reacted with E, thus obtaining D; as outlined in the following reaction scheme:

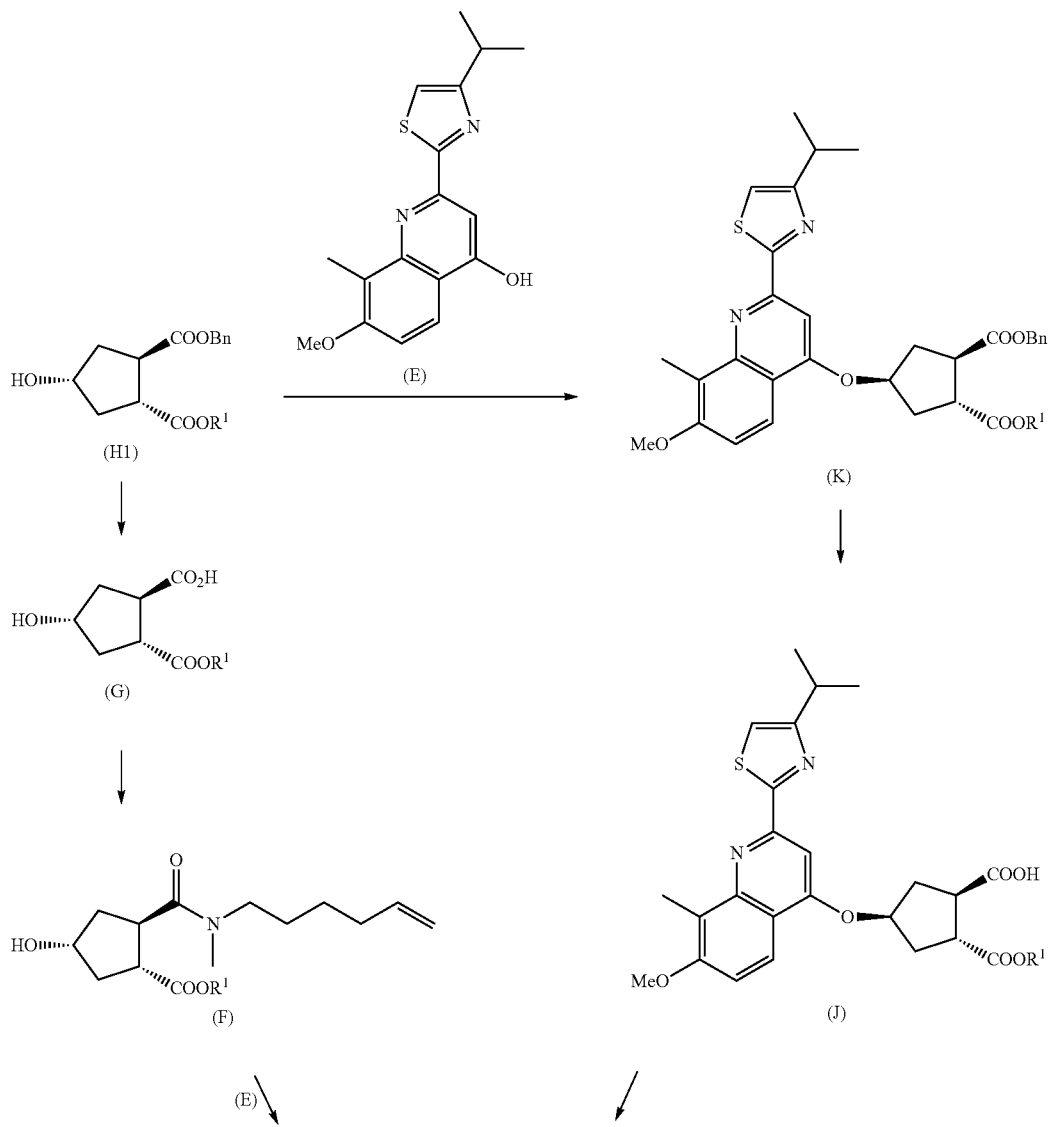

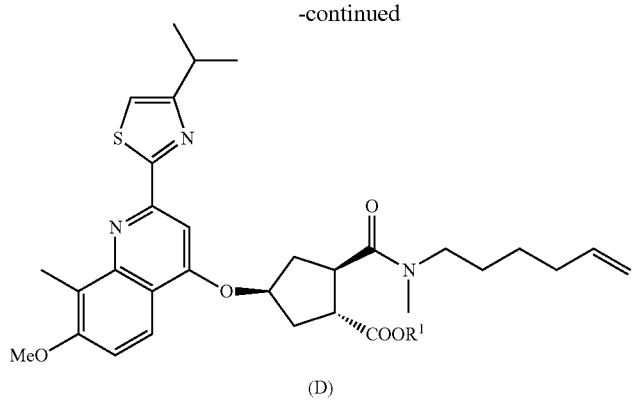

(D)

Each $R^1$ is in this scheme is as specified above and Bn represents benzyl.

WO 2008/092955 furthermore describes procedures for preparing intermediate H1 starting from 4-oxo-1,2,-cyclopentanedicarboxylic acid O, by a keto to alcohol reduction, thus obtaining 4-hydroxy-1,2-cyclopentanedicarboxylic acid N, which in turn is cyclized to the bicyclic lactone M. Esterification of the carboxylic acid group in the latter yields the lactone benzyl ester L, wherein the lactone is opened by a transesterification reaction in the presence of a $C_{1-4}$alkanol, thus yielding intermediate H, which is resolved in its enantiomers H1 and H2, as outlined in the following reaction scheme:

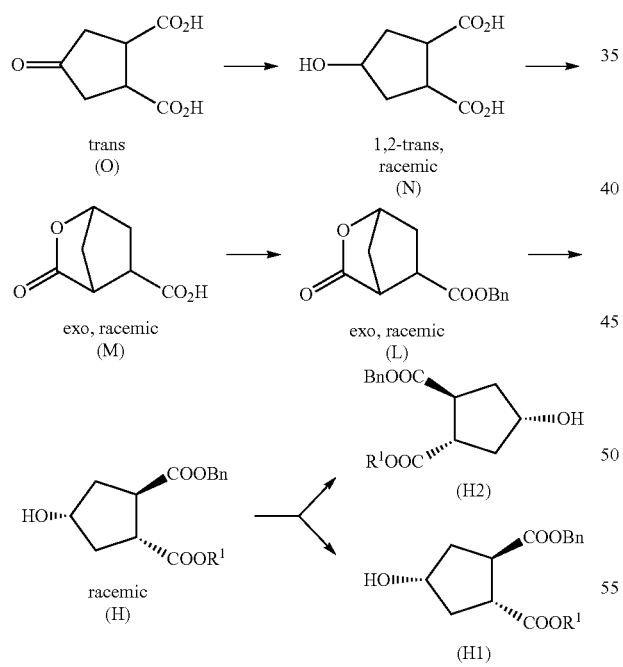

A disadvantage of the above process is that it involves a resolution of the enantiomers of H by chiral column chromatography, a cumbersome procedure that is difficult to run at large scale production. Another disadvantage is that the resolution takes place at a later stage of the synthesis, whereby half of the building block H has to be discarded. The presence of various chiral centers in the compound of formula I and its predecessors poses particular challenges in that enantiomeric purity is essential to have a product that is acceptable for therapeutic use. Hence the processes for preparing D should result in products of acceptable enantiomeric purity without use of cumbersome purification procedures with the loss of substantial amounts of undesired stereoisomeric forms.

Honda et al., Tetrahedron Letters, vol. 22, no. 28, pp 2679-2682, 1981, describes the synthesis of (+)-brefeldin A, using the following starting materials:

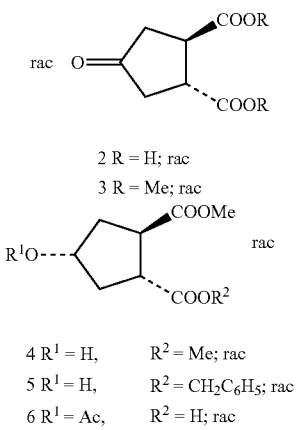

The synthesis of Honda et al. starts from dl-trans-4-oxocyclopentane-1,2-dicarboxylic acid 2, which was esterified to the corresponding methyl ester 3, and reduced with Raney-Ni to the alcohol 4. Partial hydrolysis of 4 to the monocarboxylic acid and benzylation with benzyl bromide gave predominantly diastereoisomer 5, namely the diastereoisomer wherein the hydroxy and benzyl ester groups are in cis position. The latter ester 5 in Honda et al. and compound H are both racemates, but are diastereoisomers of one another, more precisely epimers on the carbon no. 4 bearing the hydroxy group. Compound H1 is one of the two enantiomers obtained by separation from the racemic compound H. The other enantiomer is compound H2.

The bicyclic lactone (17b) is an interesting building block in the synthesis of the compound of formula I. Finding a synthesis path to obtain this lactone in good yield and high enantiomeric purity is a desirable goal to achieve. The present invention provides a process to prepare (1R,2R)-4-oxo-1,2-cyclopentanedicarboxylic acid, which can be readily converted to the bicyclic lactone (17b).

The processes of the present invention are advantageous in that they are suitable for large scale production. Cumbersome purification steps, in particular by chromatography, are avoided.

DESCRIPTION OF THE INVENTION

Overview of structures described in this description and claims.

| Compound number | Structure |
|---|---|
| II | (4-oxocyclopentane-1,2-dicarboxylic acid) |
| III | (4-oxocyclopentane-1,2-dicarboxylic acid ·2 base) |
| | (alkaloid structure with N, OMe groups) |
| IV | (4-oxocyclopentane-1,2-dicarboxylic acid ·2 base) |
| | (ephedrine: PhCH(OH)CH(CH₃)NHCH₃) |
| V | (4-oxocyclopentane-1,2-dicarboxylic acid, (±)) |
| VI | (4-hydroxycyclopentane-1,2-dicarboxylic acid) |
| VII | (bicyclic lactone-COOH) identical with (bicyclic lactone-COOH) |
| VIII | (dimethyl 4-oxocyclopentane-1,2-dicarboxylate) |
| IX | (dimethyl 4-hydroxycyclopentane-1,2-dicarboxylate, HO⋯) identical with (dimethyl 4-hydroxycyclopentane-1,2-dicarboxylate, HO-) |
| X | (methyl, benzyl 4-hydroxycyclopentane-1,2-dicarboxylate) |

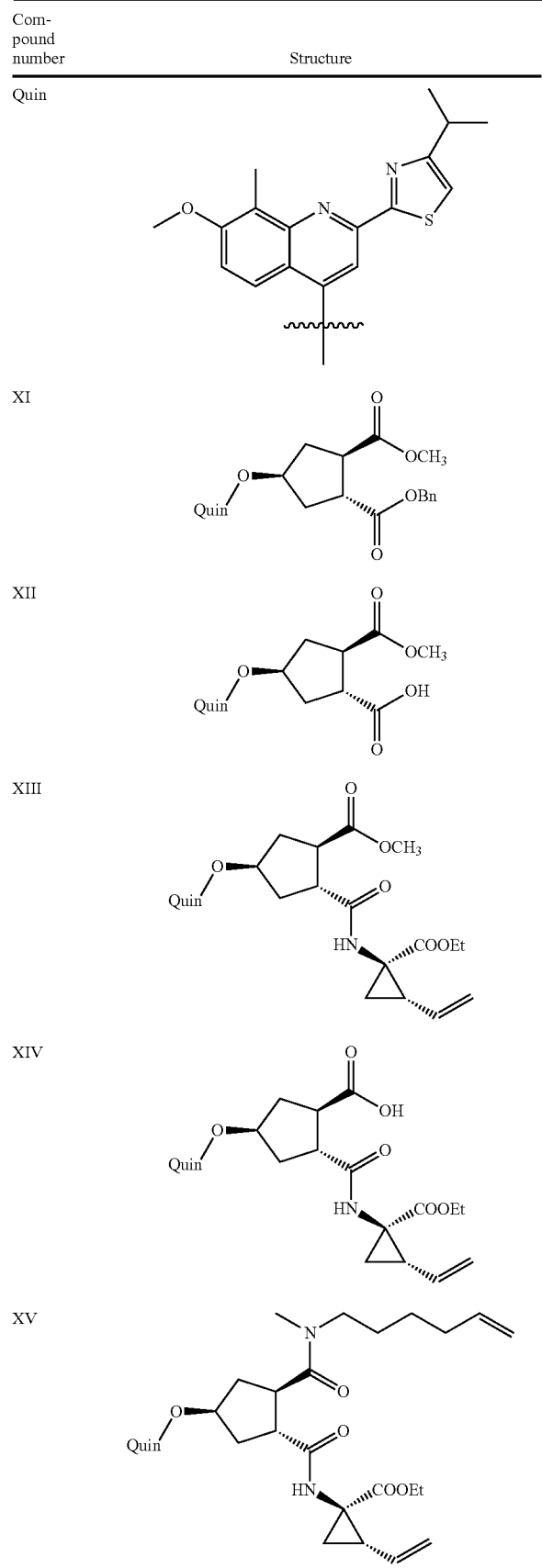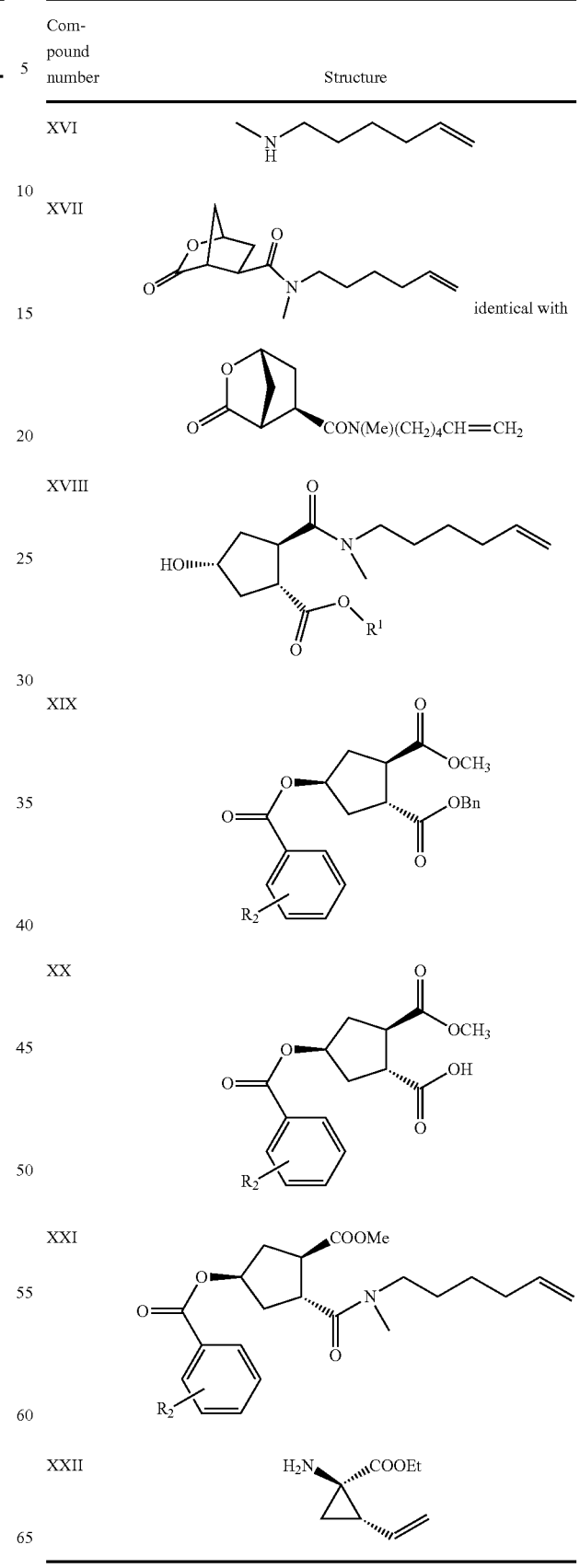

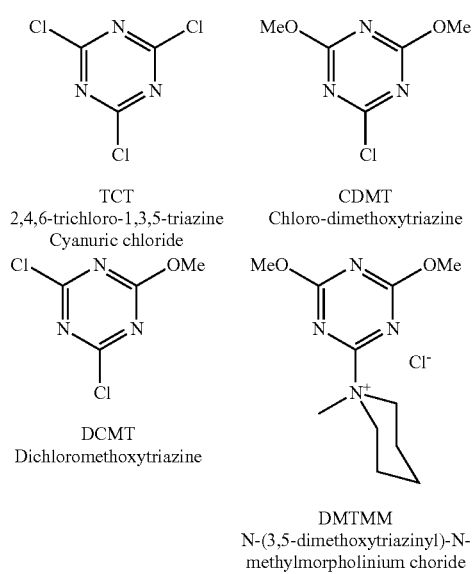

TCT
2,4,6-trichloro-1,3,5-triazine
Cyanuric chloride

CDMT
Chloro-dimethoxytriazine

DCMT
Dichloromethoxytriazine

DMTMM
N-(3,5-dimethoxytriazinyl)-N-methylmorpholinium choride

In one aspect, the present invention relates to a process for preparing [(1R,2R)-4-oxo-1,2-cyclopentanedicarboxylic acid II, by the resolution of racemic 4-oxo-1,2-cyclopentanedicarboxylic acid (V), said process comprising (a) reacting 4-oxo-1,2-cyclopentanedicarboxylic acid (V) with brucine or (1R,2S)-(−)-ephedrine, thus preparing the bis-brucine or bis-(1R,2S)-(−)-ephedrine salt of (V), and (b) precipitating selectively the bis-brucine or bis-(1R,2S)-(−)-ephedrine salt of (1R,2R)-4-oxo-1,2-cyclopentanedicarboxylic acid II, while the bis-brucine or bis-(1R,2S)-(−)-ephedrine salt of [(1S,2S)-4-oxo-1,2-cyclopentanedicarboxylic acid stays in solution;

(c) liberating the acid II by removal of brucine or (1R,2S)-(−)-ephedrine from the precipitated salt obtained in step (b).

This process is outlined in the following reaction scheme:

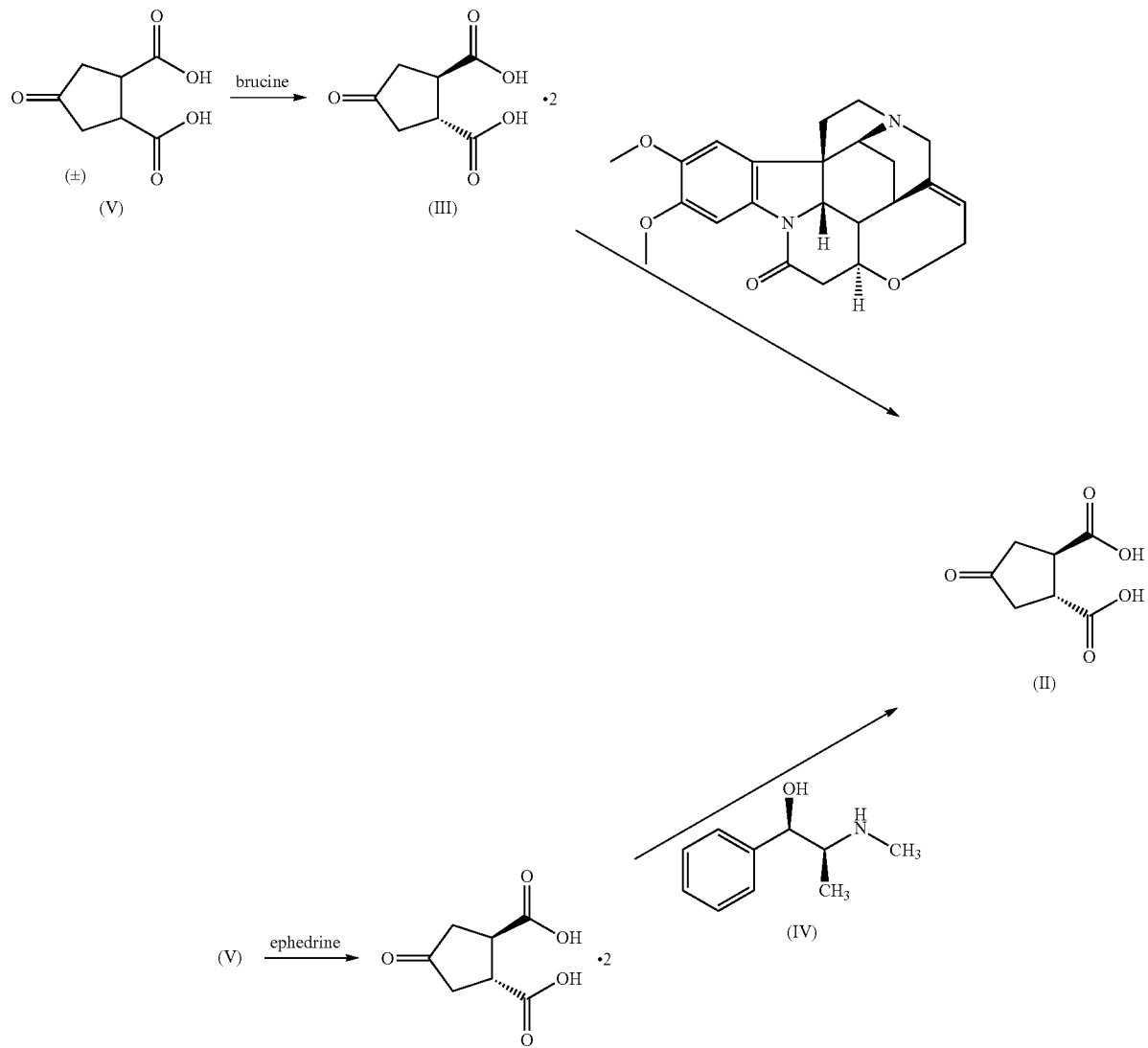

The invention also concerns the intermediate [(1R,2R)-4-oxo-1,2-cyclopentane-dicarboxylic acid salt with brucine (1:2), having the structure III, and the [(1R,2R)-4-oxo-1,2-cyclopentanedicarboxylic acid salt with (1R,2S)-(−)-ephedrine (1:2), having the structure IV.

The brucine salt III can be obtained by mixing brucine and trans-4-oxo-1,2-cyclopentanedicarboxylic acid in the presence of a solvent, heating the mixture until all solids dissolve, and allowing the mixture to cool whereby the brucine salt crystallizes. Solvents include alcohols such as methanol or ethanol and aqueous alcohols, such as aqueous methanol or ethanol. Of interest are alcohol/water mixtures with a minor amount of water, e.g. a water content in the range of about 2% to about 20%, or about 5% to about 10% (w/w). In particular, use can be made of a mixture of water/methanol with a water content in the range of about 5% to about 10%, e.g. about 5% (w/w). In one embodiment a mixture of aqueous alcohol and brucine is made and slightly heated to a temperature in the range of about 30° C. to about 50° C., e.g. at about 40° C. whereupon a solution of trans-4-oxo-1,2-cyclopentanedicarboxylic acid is added. The resulting mixture is heated until all solids are dissolved, in particular by heating to reflux temperature. Then the mixture is allowed to cool, preferably slowly, to room temperature. The solids that are formed are filtered. They may be recrystallized, e.g. from water.

The (1R,2S)-(−)-ephedrine salt IV can be obtained similarly, but instead of aqueous alcohols, aqueous ketones such as aqueous acetone can be used. Of interest are acetone/water mixtures with a minor amount of water, e.g. a water content in the range of about 2% to about 25%, or about 10% to about 20% (w/w), e.g. about 16% (w/w).

The resolution can also be performed with (1S,2R)-(+)-ephedrine yielding the (1S,2S)-4-oxo-1,2-cyclopentanedicarboxylic acid (1S,2R)-(+)-ephedrine (2:1) salt as a white solid.

The resolution of trans-4-oxo-1,2-cyclopentanedicarboxylic acid was also attempted with cinchonidine, resulting in the [(1S,2S)-4-oxo-1,2-cyclopentanedicarboxylic acid cinchonidine (1:2)] salt being isolated as a solid.

Resolution was also attempted with cinchonine however the salt, in its racemic form, could only be isolated as a glassy solid.

Resolution was also attempted with nicotine, again unsuccessfully as the salt of trans-4-oxo-1,2-cyclopentanedicarboxylic acid was isolated as an oil.

The brucine and (1R,2S)-(−)-ephedrine salts of (1R,2R)-4-oxo-1,2-cyclopentanedicarboxylic acid can be converted to the free acid of formula II. In a first step brucine and (1R,2S)-(−)-ephedrine are removed by treating aqueous suspensions of the salts with a base, e.g. ammonium hydroxide. This is preferably done at increased temperature, for example at a temperature that is in the range of 60° C. to 100° C., e.g. at 80° C. Cooling to room temperature results in crystallization of solid brucine, which can be isolated by filtration. Work-up of the remaining solution can be done by evaporation to dryness, and re-dissolution of the residue in water. To this solution, an acid was added, e.g. HCl, resulting in the precipitation of (1R,2R)-4-oxo-1,2-cyclopentane-dicarboxylic acid. The resulting solids can be filtered and washed with cold water.

The bisalkali metal salt form of II can also be prepared and isolated.

The recovered brucine can be dried and recrystallized from water-ethanol (50:50) to purify the brucine, which can be re-used in the resolution.

In further aspect, the (R,R)-4-oxo-1,2-cyclopentanedicarboxylic acid II, obtained by the above process, or the brucine salt III or the (1R,2S)-(−)-ephedrine salt (IV), are used as a starting material in a process for preparing the bicyclic lactone (VII), by reducing the keto functionality to an alcohol resulting in 4-hydroxy-1,2-cyclopentane-dicarboxylic acid (VI), which is cyclized to the lactone (VII).

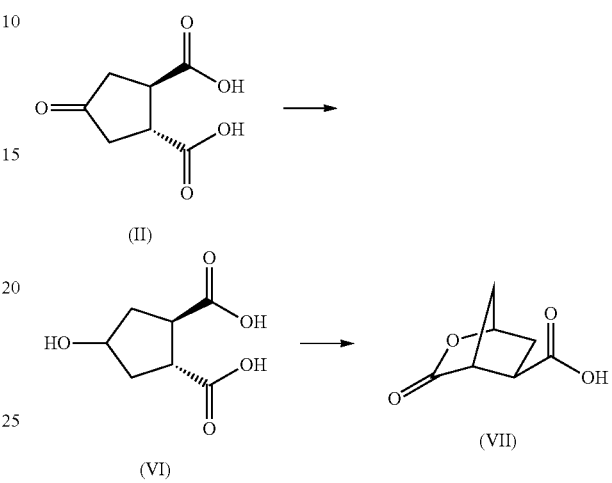

The racemic 4-oxo-1,2-cyclopentanedicarboxylic acid V starting material can be prepared as described above in the Background of the Invention section. The keto to hydroxy reduction in II to VI can be done using a suitable reductant, in particular by hydrogen in the presence of a metal catalyst, e.g. rhodium on carbon or on alumina or Raney Ni, in a reaction-inert solvent, e.g. in an aqueous medium, such as water, in the presence of a base, e.g. NaOH, KOH, or an organic base such as triethylamine, N-methylmorpholine or Hunig's base (diisopropylethylamine).

The resulting 4-hydroxycyclopentane-1,2-dicarboxylic acid VI can be converted to a salt, e.g. a bistertiary amine salt such as the bis-triethylamine salt, or a bisalkali metal salt such as the bis sodium or bis potassium salts.

Intermediate VI can be cyclized to form the lactone VII by reaction with a chloroformate, e.g. with ethyl or methyl chloroformate. This reaction can be conducted in a reaction-inert solvent such as a ketone, in particular acetone, or an ether such as THF or MeTHF, or acetonitrile. A base can be added, e.g. a tertiary amine such as triethylamine or N-methylmorpholine (NMM). In an alternative embodiment the lactone-forming agent is 2,4,6-trichloro-1,3,5-triazine (TCT) or a derivative thereof.

In a particular embodiment, intermediate II is converted to the 4-hydroxy-1,2-cyclo-pentane-dicarboxylic acid VI by a reduction reaction as described above, which is cyclized to the lactone VII using a triazine derivative, in a one-pot procedure without isolation of intermediary products. VI is obtained in water after the reduction step, to which an organic co-solvent might be added in the second step, for example acetone, methylethylketone (MEK), tetrahydrofuran (THF) or 2-methyltetrahydrofuran (MeTHF). Triazine derivatives for this reaction comprise agents such as 2,4,6-trichloro-1,3,5-triazine (TCT), chloro-dimethoxytriazine (CDMT), N-(3,5-dimethoxy-triazinyl)-N-methylmorpholinium chloride (DMTMM) or dichloromethoxytriazine (DCMT). This reaction sequence offers a simple, short and economic procedure to prepare the lactone VII in high yield and purity. The water used as solvent in the reduction step need not removed and no separation of the intermediate 4-hydroxy-1,2-cyclopentane-dicarboxylic acid VI is necessary.

The brucine and (1R,2S)-(−)-ephedrine salts of (1R,2R)-4-oxo-1,2-cyclopentane-dicarboxylic acid III or IV can be converted directly to the dimethyl (1R,2R)-4-oxo-1,2-cyclopentanedicarboxylate ester. In a first step brucine and (1R,2S)-(−)-ephedrine are removed as described above and solid brucine and (1R,2S)-(−)-ephedrine are isolated. The mother liquors after the recovery of brucine and (−)-ephedrine are evaporated to yield enantiomerically pure (1R,2R)-4-oxo-1,2-cyclopentanedicarboxylic acid. This can be used to make I as described in WO 2007/014926. Thus, the residue that is obtained after evaporation is taken up in a methanol/toluene mixture and a strong acid, e.g. sulfuric acid is added. The reaction mixture is heated up, preferably to reflux, whereafter the solvent is distilled off from the reaction mixture until an internal temperature of >70° C. is reached. The mixture is then cooled to about 30° C. and water added. The resulting mixture is stirred at room temperature and further worked up by isolating the organic layer that is formed. Evaporation yields the desired dimethyl ester.

The latter can be converted to dimethyl (1R,2R)-4-oxo-1,2-cyclopentanedicarboxylate ester VIII as described above and further converted to other intermediates in the synthesis of the compound of formula I. The keto group in VIII is reduced yielding an intermediate IX, which is converted to X by a hydroxy-assisted transesterification reaction. The hydroxy-function in X is converted to a quinolinyl ether group in XI with a Mitsunobu reaction, which involves an inversion at the hydroxy-bearing carbon atom. The benzyl group in XI is removed, subsequently yielding an intermediate XII, and the latter is coupled with a cyclopropyl amino acid ester XXII to give XIII, in which the methyl ester is hydrolyzed to yield XIV. The latter is coupled with N-methyl-5-hexen-1-amine XVI resulting in an intermediate XV, which is as described above and can be cyclized to macrocyclic intermediate A, which is converted to end product I.

This reaction sequence is illustrated in the following scheme wherein Quin represents a quinoline group of formula:

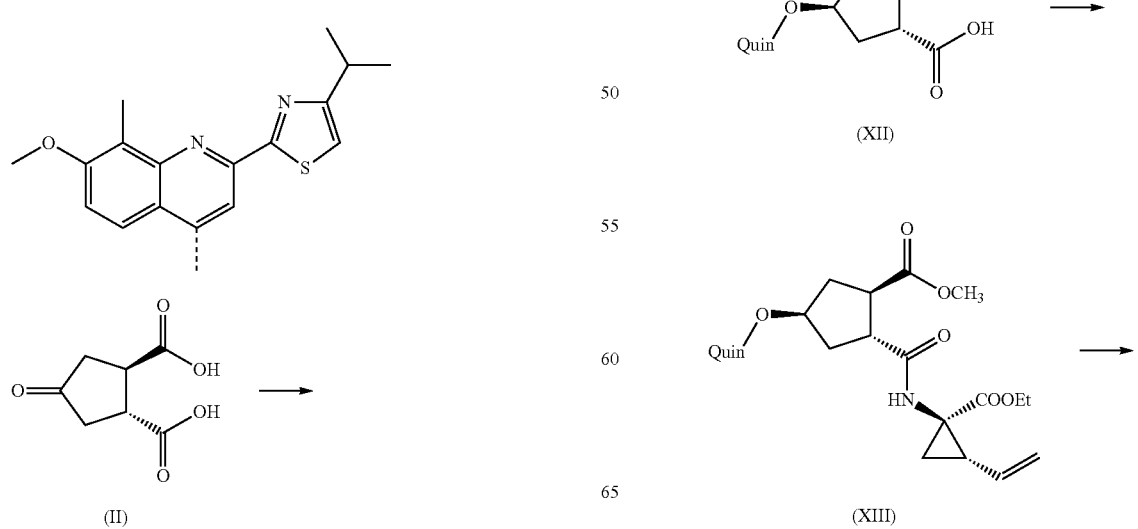

-continued (XIV)

(XV)

This synthesis procedure offers the advantage that several intermediates can be crystallized, allowing to eliminate impurities. The end product is obtained in high yield and purity, in particular high stereochemical purity. Intermediates that can be isolated as a solid are intermediates XI, XII, XIII and XIV.

In a further aspect, compound XVIII, a useful intermediate to prepare I, is obtained from intermediate X via the route described below:

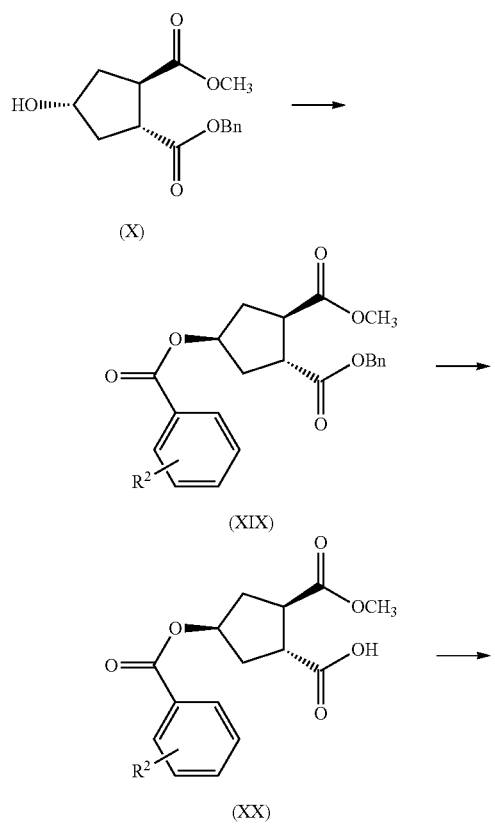

(X)

(XIX)

(XX)

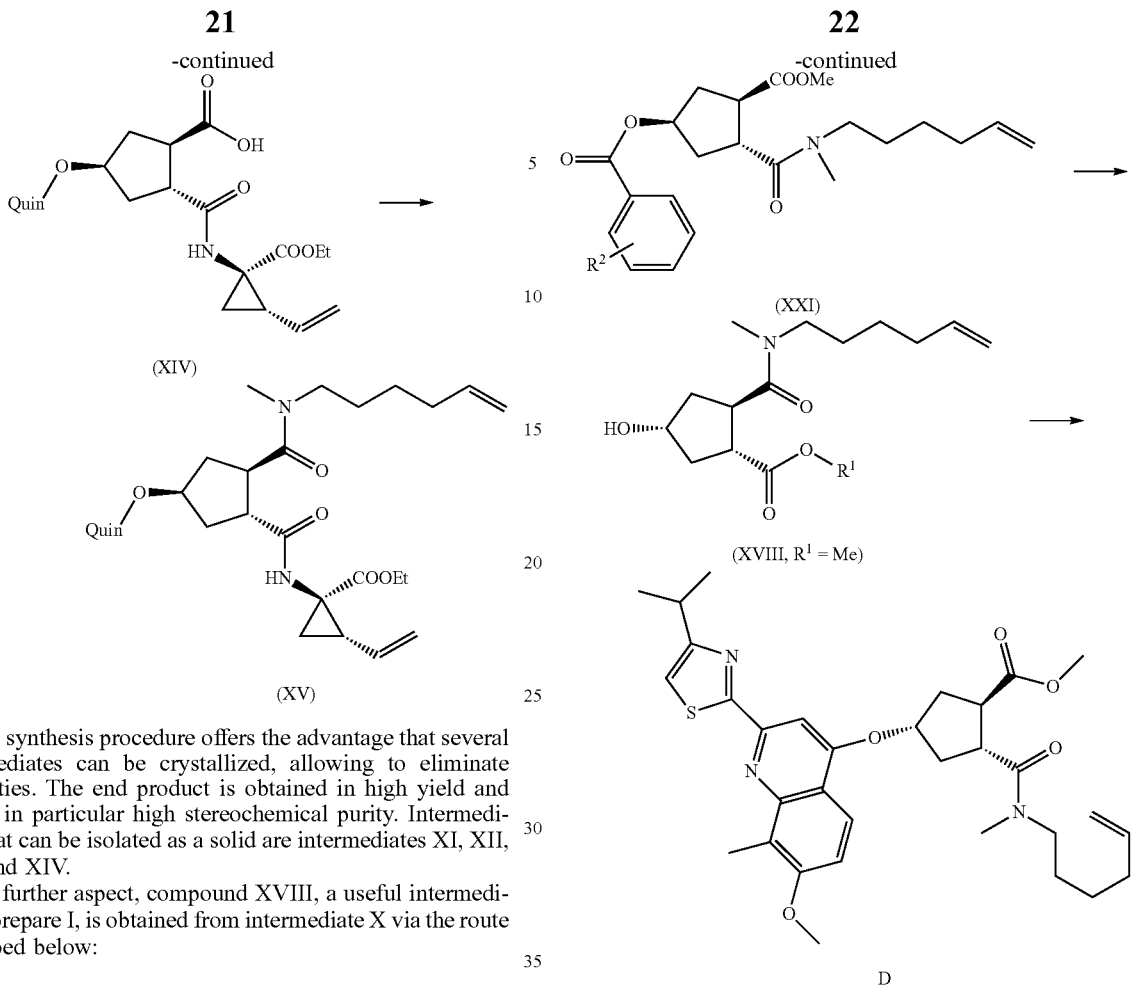

-continued (XXI)

(XVIII, $R^1$ = Me)

D

In the above scheme and hereinafter, $R^2$ is hydrogen, $C_{1-4}$alkyl, aryl, halogen, $-SO_2-C_{1-4}$alkyl, CN, or $NO_2$. $R^2$ can be substituted in o, m, or in particular in p-position. Of interest is $NO_2$, in particular p-$NO_2$ (4-$NO_2$). $R^1$ is as specified above and in particular is methyl.

Compound X is reacted with an aromatic acid, an azodicarboxylate and a phosphine in a Mitsunobu reaction to give XIX, which is isolated as a crystalline solid from the reaction mixture, thereby providing an efficient purification from both impurities in X and those from the Mitsunobu reaction, as well. XIX is treated with palladium acetate and sodium formate to give XX, which is coupled with N-methyl-5-hexen-1-amine XVI to give XXI, which is treated with a base in methanol to give XVIII (R'=Me).

The synthesis procedures of the present invention offers the advantage that the correct stereochemistry at the cyclopentane moiety is obtained without using chiral chromatography. The brucine salt III and the ephedrine salt IV have been found to selectively crystallize with high diastereomeric purity (containing the acid II in high enantiomeric purity).

The finding that the salts III and IV can be isolated by crystallization provides an elegant way to obtain (R,R)-4-oxo-1,2-cyclopentanedicarboxylic acid II and eventually the bicyclic lactone VII in high enantiomeric purity. Recrystallization or reslurrying allows further purification of these salts. The salts III and IV can be used as starting material in the further synthesis of the acid VI, as described above. The latter in turn can be converted to the lactone VII, an important building block in the preparation of the compound of formula I.

In another embodiment, the present invention relates to the compounds per se of formula III or IV.

The cyclic lactone acid VII can be isolated, either as an acid or a salt thereof, but the resulting aqueous-organic solution of VII obtained in the reaction sequence described above can be used directly in a coupling reaction with the amine XVI to obtain the amide XVII.

In further aspect, the bicyclic lactone acid VII, or a salt thereof, either isolated or non-isolated, is used as a starting material in a process for preparing the cyclopentane derivative XVIII, by reacting the bicyclic lactone VII with N-methyl-5-hexen-1-amine (NMHA) XVI in an amide-forming reaction to yield the bicyclic lactone amide XVII, in which the lactone group is opened to yield the desired product XVIII. These reactions are illustrated in the scheme below, wherein $R^1$ is as specified above.

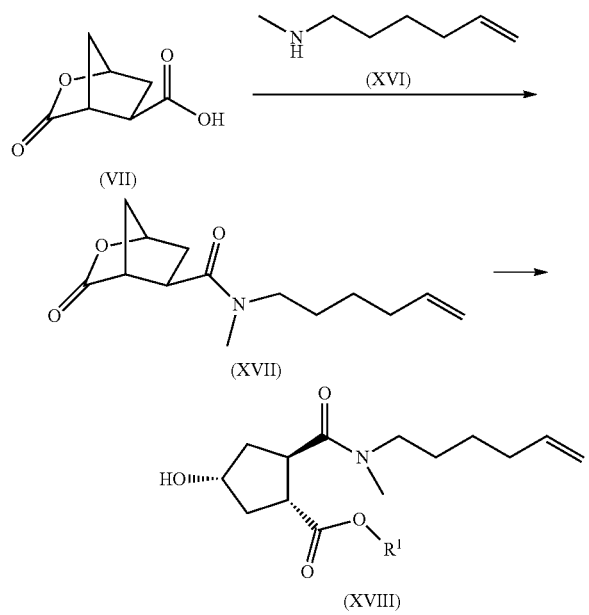

The further processing of the compound of formula XVIII to the end products of formula I are as outlined in the reaction schemes above and in particular as described in WO 2008/092955. The reaction of the bicyclic lactone VII with N-methyl-5-hexen-1-amine XVI is an amide forming reaction, which comprises reacting the starting materials with an amide-coupling reagent in a solvent, optionally in the presence of a base, as described in WO 05/073195 and WO 2007/014926. This reaction can be conducted, for example, by using N-ethoxycarbonyl-2-ethoxy-1,2-dihydroquinoline (EEDQ) as coupling agent, in dichloromethane (DCM), tetrahydrofuran (THF) or 2-methyltetrahydrofuran (MeTHF) as solvent, or can be performed by using TCT or a derivative thereof (CDMT, DCMT, DMTMM) in water or a mixture of water and an organic solvent. Organic solvents to this purpose include acetone, methylethylketone (MEK), tetrahydrofuran (THF), MeTHF, CPME (cyclopentyl methyl ether), $C_{1-4}$alkyl acetate, $C_{1-4}$alkyl propionate, $C_{1-4}$alkyl butyrate and toluene.

As used in the foregoing and hereinafter, the following definitions apply unless otherwise noted. The term "$C_{1-4}$ alkyl" defines straight or branched chain saturated hydrocarbon radicals having from 1 to 4 carbon atoms such as for example methyl and ethyl; and also 1-propyl, 2-propyl, 1-butyl, 2-butyl, 2-methyl-1-propyl, 2-methyl-2-propyl.

The generally accepted convention for representing stereochemical compounds, which is also adhered to herein is the following:
- A compound represented without stereobonds, is racemic or the configuration of the stereogenic center(s) is not defined.
- A compound represented with stereobonds and one of the descriptors "(±)", "rel", or "rac", is racemic and the stereochemistry is relative.
- A compound represented with stereobonds but without the descriptors "(±)", "rel", or "rac" refers to a non-racemic compound (scalemic substance) i.e. enantio-enriched.

For instance, in the Honda et al. reference the designation "(±)" is used in the title of the article, meaning that there is described a racemic synthesis with racemic intermediates. However the above convention may not necessarily be followed in all publications.

The enantiomeric purity is given as enantiomeric ratio (e.r.). For the salts, the e.r. value refers to the ratio of the two enantiomers of the acid in the mixture of diastereomeric salts.

EXAMPLES

The following examples are intended to illustrate the present invention and should not be construed as a limitation of the scope of the present invention.

Example 1

Resolution of 4-Oxo-1,2-Cyclopentanedicarboxylic Acid with Brucine

Preparation of 4-oxo-1,2-cyclopentanedicarboxylic acid bis brucine salt, i.e. (1R,2R)-4-oxo-1,2-cyclopentanedicarboxylic acid salt with brucine (1:2)

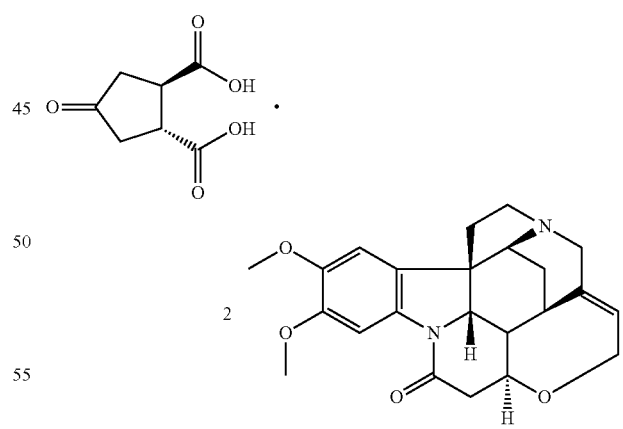

Brucine (288.7 g, 0.73 mol) was added to a solution of water (87 ml) in methanol (1653 ml). The mixture was heated to 40° C. and a solution of rac-trans-4-oxo-1,2-cyclopentanedicarboxylic acid (60 g, 0.35 mol) in methanol (665 ml) and water (35 ml) was added dropwise over 15 minutes. The resulting suspension was heated to reflux until all solids had dissolved. The mixture was allowed to cool slowly to 22° C. The solids were filtered and washed with a little water. The solid material was dried under vacuum at 50° C. for 16 hours to yield 265 g of the brucine salt (approximately 1:1 mixture of diastereomers). This salt was then recrystallized from water (1026 ml) to yield after drying 120.6 g (36%) of (1R,2R)-4-oxo-1,2-cyclopentanedicarboxylic acid compound with brucine (1:2) as an off white crystalline solid.

$[\alpha]_D$: −91.4

Example 2

Resolution of 4-oxo-1,2-cyclopentanedicarboxylic acid with (−)-ephedrine

Preparation of 4-oxo-1,2-cyclopentanedicarboxylic acid bis ephedrine salt, i.e. (1R,2S)-(−)-ephedrine [(1R,2R)-4-oxo-1,2-cyclopentanedicarboxylic acid compound with (1R,2S)-(−)-ephedrine (1:2)]

(1R,2S)-(−)-ephedrine (20.16 g, 0.12 mol) was added to a suspension of trans-4-oxo-1,2-cyclopentanedicarboxylic acid (10 g, 58 mmol) in acetone (200 ml) and water (26 ml). The mixture was heated to reflux until a homogeneous solution was formed. Allow the mixture to cool slowly to 22° C. The solids were filtered and washed with acetone. The solid material was dried under vacuum at 50° C. to yield 10.3 g (35%) of (1R,2R)-4-oxo-1,2-cyclopentanedicarboxylic acid compound with (1R,2S)-(−)-ephedrine (1:2) as a white solid.

$[\alpha]_D$: −69.1

1H-NMR (400 MHz, DMSO-d6) δ ppm 0.86 (d, J=6.8 Hz, 6H) 2.29-2.39 (m, 1H) 2.39-2.47 (m, 1H) 2.49 (s, 6H) 2.96-3.12 (m, 4H) 4.89 (d, J=3.3 Hz, 2H) 7.19-7.32 (m, 2H) 7.33-7.54 (m, 8H). 13C-NMR (150 MHz, DMSO-d6) 11.17, 31.81, 42.12, 44.06, 59.55, 71.08, 125.97, 126.92, 127.93, 142.17, 175.74, 176.47, 215.40.

The resolution can also be performed with (1S,2R)-(+)-ephedrine to yield in 32% yield (1S,2S)-4-oxo-1,2-cyclopentanedicarboxylic acid compound with (1S,2R)-(+)-ephedrine (1:2) as a white solid.

$[\alpha]_D$: +66.3

Example 3

(1R,2R)-4-oxo-1,2-cyclopentanedicarboxylic acid and recovery of ephedrine

To a solution of (1R,2R)-4-oxo-1,2-cyclopentanedicarboxylic acid salt with (1R,2S)-(−)-ephedrine (1:2) (251 g, 0.5 mol) was added 8 N aqueous KOH (199.21 g, 1.10 mole) and the mixture was stirred for 5 minutes. 2-Methyltetrahydrofuran (688 ml) was added and the mixture was stirred vigorously for 20 minutes. The two layers were separated and the aqueous phase was acidified with HCl. The 2-methyltetrahydrofuran organic phase contained the ephedrine, which could be recycled from that phase. The aqueous phase was then evaporated to dryness on the rotavapor and the residue recrystallized from water (50 ml) to yield 55.15 g (64% yield) of (1R,2R)-4-oxo-1,2-cyclopentane-dicarboxylic acid as an off white solid.

The 2-methyltetrahydrofuran solution of ephedrine was evaporated to dryness on the rotavapor to yield crude ephedrine as a yellow oil, which solidified on standing after 3 days. The crude ephedrine was dissolved in 2-methyltetrahydrofuran (400 ml) and the mixture made acidic with HCl in isopropanol. The solid material was filtered and washed with 2-methyltetrahydrofuran (50 ml). The solid ephedrine hydrochloride was dried under vacuum at 50° C. before being dissolved in water (300 ml) at 40° C. Sufficient potassium carbonate was added portionwise to the warm aqueous solution, until a two-phase system was obtained. 2-Methyltetrahydrofuran (200 ml) was added and the mixture stirred vigorously for 5 minutes. The two layers were separated and the aqueous phase extracted with 2-methyltetrahydrofuran (200 ml). The combined organic layers were dried over $Na_2SO_4$, filtered and evaporated to dryness to yield 124.7 g (75% yield) of recovered ephedrine as a white solid.

Example 4

Preparation of Bicyclic Lactone Carboxylic Acid VII

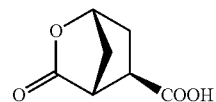

(VII)

To a suspension of 32.7 g (0.19 mol) of (1R,2R)-4-oxo-1,2-cyclopentanedicarboxylic acid (intermediate II) in 237.5 ml water under an atmosphere of nitrogen was added 1.0 ml (0.019 mol) 50% wt/wt aqueous NaOH. The mixture was warmed to 60° C. and 2.5 g Rh/C (5% wt/wt) were added. Then the reaction flask was purged with hydrogen and kept under an atmosphere of hydrogen while stirring until complete conversion was reached. The warm reaction mixture was filtered over Celite and the filter cake washed twice with 10 ml water. Triethylamine (55.61 ml, 0.40 mol) was added and 80% of the solvent volume was distilled off under a pressure of 30 mbar. The reaction flask was fitted with a Dean-Stark trap filled with 2-methyltetrahydrofuran and 2-methyltetrahydrofuran (100 ml) was added to the reaction mixture. The mixture was refluxed for 4 hours to remove the remaining water. Then 80% of the solvent volume was distilled off under ambient pressure. The mixture was cooled to 50° C. and acetone (380 ml) was added. The mixture was cooled further to 22° C. and additional acetone (760 ml) was added. The resulting suspension was cooled under an atmosphere of nitrogen to −5° C. and triethylamine added (27.8 ml, 20.24 g, 0.2 mol). Subsequently, ethyl chloroformate (22.68 g, 0.21 mol) was added drop-wise and the mixture was stirred at 0° C. for 3 hours, then at 22° C. for a further 12 hours. The reaction mixture was filtered over Dicalite and the solids washed with acetone (100 ml). The resulting solution of VII in acetone could be used in further procedures to prepare intermediate XVII.

Example 5

Synthesis of VIII, dimethyl (1R,2R)-4-oxo-1,2-cyclopentanedicarboxylate

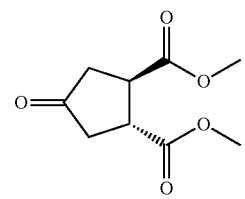

A suspension of 4-oxo-1,2-cyclopentanedicarboxylic acid bis brucine salt (144 g, 0.15 mol) in water (750 ml) was heated to 80° C. Ammonium hydroxide (50% solution in water, 11.8 ml, 0.32 mol) was added dropwise and the resulting mixture was stirred at 80° C. for 30 minutes. The suspension was cooled to 22° C. and filtered, the solid material was then washed with water (37 ml). The combined filtrate and washings were evaporated to dryness on the rotavapor. To the residue was added methanol (300 ml) and toluene (750 ml). Sulfuric acid (4.3 ml) was added and the mixture heated to reflux for 2 hours. Solvent was distilled of from the reaction until an internal temperature of >70° C. was reached. The mixture was cooled to 30° C. and water (150 ml) was added. The resulting mixture was stirred at 22° C. for 60 minutes. The two layers were separated and the organic phase was dried over $Na_2SO_4$, filtered and evaporated to dryness to yield 27 g of dimethyl (1R,2R)-4-oxo-1,2-cyclopentanedicarboxylate as a pale yellow oil which solidified on standing.

GC-MS: m/z=200 (M+). $^1$H-NMR (600 MHz, $CDCl_3$) δ ppm 2.35-2.40 (m, 2H) 2.50-2.56 (m, 2H) 3.25-3.31 (m, 2H) 3.75 (s, 6H)). $^{13}$C-NMR (150 MHz, $CDCl_3$) δ0.56, 43.23, 52.09, 172.87, 212.03.

$[α]_D$: −192.2

Example 6

Synthesis of IX, dimethyl (1R,2R)-4-hydroxy-1,2-cyclopentanedicarboxylate

Rhodium on alumina (5% wet, 25 g) was added to a solution of dimethyl (1R,2R)-4-oxo-1,2-cyclopentanedicarboxylate (100 g, 0.5 mol) in tetrahydrofuran (1000 ml). The reaction vessel was purged with hydrogen and then stirred under an atmosphere of hydrogen until complete conversion. The reaction mixture was filtered over Dicalite and the filter cake washed with tetrahydrofuran (10 ml). The combined filtrate and washings were evaporated to dryness to yield 95.9 g of dimethyl (1R,2R)-4-hydroxy-1,2-cyclopentanedicarboxylate as a colourless oil.

This reduction could also be carried out using Raney-Ni as catalyst under hydrogen at 6 bar pressure.

Example 7

Synthesis of intermediate X, benzyl methyl (1R,2R,4R)-4-hydroxy-1,2-cyclopentanedicarboxylate

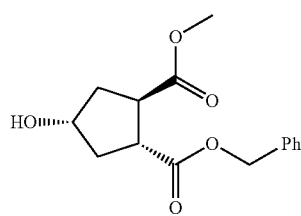 [SMILES: COC(=O)[C@@H]1C[C@@H](O)C[C@H]1C(=O)OCc1ccccc1]

Toluene (435 ml), sodium carbonate (23.6 g, 0.22 mol) and benzyl alcohol (48.13 g, 0.45 mol) were added to a flask fitted with a Dean-stark trap. The mixture was heated to reflux for 90 minutes to remove any traces of water. The mixture was cooled to 80° C. and the reaction flask purged with nitrogen. Dimethyl (1R,2R)-4-hydroxy-1,2-cyclopentanecarboxylic acid (30 g, 0.15 mol) was added and the mixture was heated to reflux with a slight flow of nitrogen over the reaction mixture for 6 hours. A solution of HCl (42 ml, 0.46 mol) in water (56 ml) was added dropwise and the mixture was stirred at 22° C. for 15 minutes. The two layers were separated and the aqueous phase was extracted with toluene (30 ml) and dichloromethane (30 ml). The combined organic layers were dried over $Na_2SO_4$, filtered and evaporated to dryness on the rotavapor to obtain crude intermediate X.

The residue was purified by chromatography over silica gel eluting with $CH_2Cl_2$/ethyl acetate (85:15) to yield 23.9 g (58% isolated yield) of benzyl methyl (1R,2R,4R)-4-hydroxy-1,2-cyclopentanedicarboxylate as a colourless oil.

GC-MS: m/z=278 (M+). $^1$H-NMR (600 MHz, $CDCl_3$) δ ppm 1.90-2.02 (m, 2H) 2.10-2.16 (m, 1H) 2.26 (ddd, 1H) 2.37 (d, J=4.91 Hz, 1H) 3.25-3.29 (m, 1H) 3.45 (q, J=4.9 Hz, 1H) 3.66 (s, 3H) 4.37-4.40 (m, 1H) 5.15 (s, 2H) 7.30-7.37 (m, 5H).

$^{13}$C-NMR (150 MHz, $CDCl_3$) δ8.59, 39.82, 45.21, 45.49, 52.12, 66.91, 72.86, 128.05, 128.28, 128.58, 135.73, 175.21

Example 8

Synthesis of XI, benzyl methyl (1R,2R,4S)-4-([2-(4-isopropyl-1,3-thiazol-2-yl)-7-methoxy-8-methyl-4-quinolinyl]oxy)-1,2-cyclopentanedicarboxylate

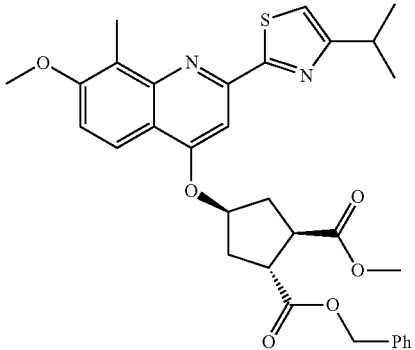

A solution of benzyl methyl (1R,2R,4R)-4-hydroxy-1,2-cyclopentanedicarboxylate (intermediate X, 4.1 g, 14.7 mmole), 2-(4-isopropyl-1,3-thiazol-2-yl)-7-methoxy-8-methyl-4(1H)-quinolinone (Quin-OH, 4.40 g, 14.0 mmole) and triphenylphosphine (5.80 g, 22.1 mmole) in toluene (74 ml) was heated to reflux under Dean-Stark conditions for 90 minutes. The mixture was cooled to −5° C. and diisopropyl azodicarboxylate (4.47 g, 22.1 mmole) was added dropwise at such a rate that the temperature remained under 5° C. The reaction mixture was stirred at 0 to 5° C. for 3 hours before being allowed to warm slowly to 22° C. and stir for 16 hours. Water (14.7 ml) was added and the mixture stirred for 10 minutes. The reaction mixture was filtered and the solids washed with a little toluene. The two phases of the filtrate were separated and the organic phase evaporated to dryness. To the residue was added 1-butanol (74 ml) and the resulting solution stirred at 22° C. for 2 hours. Solids were filtered and washed with 1-butanol (5 ml) to yield after drying 6.8 g of benzyl methyl (1R,2R,4S)-4-([2-(4-isopropyl-1,3-thiazol-2-yl)-7-methoxy-8-methyl-4-quinolinyl]-oxy)-1,2-cyclopentanedicarboxylate as a white solid.

$^1$H-NMR (600 MHz, $CDCl_3$) δ ppm 1.38 (d, J=7.1 Hz, 6H) 1.68 2.26-2.31 (m, 1H) 2.47-2.49 (m, 1H) 2.56-2.64 (m, 2H) 2.69 (s, 3H) 3.19 (hept, J=6.8 Hz, 1H) 3.35-3.39 (m, 1H) 3.57 (s, 3H) 3.68-3.72 (m, 1H) 3.97 (s, 3H) 5.18 (AB J=12.5 Hz, 2H) 5.27-5.34 (m, 1H) 7.01 (s, 1H) 7.21 (d, J=9.1 Hz, 1H) 7.30-7.39 (m, 5H) 7.44-7.49 (m, 1H) 7.94 (d, J=9.1 Hz, 1H) $^{13}$C-NMR (150 MHz, $CDCl_3$) 9.89, 22.50, 31.11, 35.92, 36.79, 45.32, 45.73, 52.21, 56.25, 66.86, 78.26, 95.70, 112.34, 114.20, 116.81, 120.28, 121.92, 128.16, 128.34, 128.48, 132.08, 135.71, 148.71, 151.80, 158.13, 160.57, 164.97, 169.93, 174.06.

mp: 112.4° C.

[α]D: −19.6

HRMS: 575.22095-mass fits with formula $C_{32}H_{35}N_2O_6S$
Calculated mass: 575.22158

Example 9

Synthesis of XII, (1R,2R,4R)-4-[[2-(4-isopropyl-1,3-thiazol-2-yl)-7-methoxy-8-methyl-4-quinolinyl]oxy]-2-(methoxycarbonyl)cyclopentanecarboxylic acid

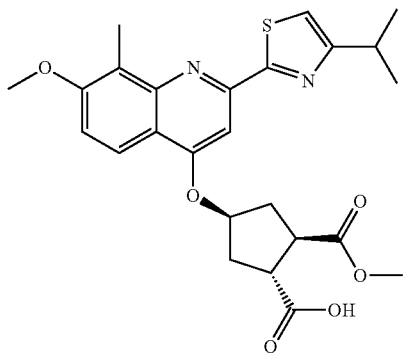

Palladium (II) acetate (152 mg, 0.68 mmol) was added to a solution of benzyl methyl (1R,2R,4S)-4-([2-(4-isopropyl-1,3-thiazol-2-yl)-7-methoxy-8-methyl-4-quinolinyl]-oxy)-1,2-cyclopentanedicarboxylate (XI, 7.8 g 13.6 mmol) in 2-methyltetrahydrofuran (27 ml) under a nitrogen atmosphere. The mixture was warmed to 45° C. and triethylsilane (6.52 ml, 40.7 mmol) was added. The resulting mixture was heated to 60° C. and stirred for 16 hours. Hydrochloric acid (115 mg, 1.1 mmol), activated charcoal (0.4 g) and Celite® (0.4 g) were added and the mixture stirred a further 60 minutes at 60° C. The reaction mixture was filtered warm and the solids washed with 2-methyltetrahydrofuran (6.8 ml). The combined filtrate and washings were evaporated to dryness. The residue was dissolved in methanol and heated to reflux. Water (13.6 g) was added and the mixture brought back to reflux. The mixture was allowed to cool slowly to 22° C. and the solid material filtered and washed with cold methanol (5.5 ml). The solids were dried under vacuum at 50° C. to yield 5.6 g of (1R,2R,4R)-4-[[2-(4-isopropyl-1,3-thiazol-2-yl)-7-methoxy-8-methyl-4-quinolinyl]oxy]-2-(methoxycarbonyl)-cyclopentanecarboxylic acid as a white solid.

$^1$H-NMR (400 MHz, CDCl$_3$) δ ppm 1.39 (d, J=6.8 Hz, 6H) 2.30-2.39 (m, 1H) 2.48-2.69 (m, 2H) 2.70 (s, 3H) 3.16-3.29 (m, 1H) 3.36-3.44 (m, 1H) 3.64 (s, 3H) 3.69-3.77 (m, 1H) 3.99 (s, 3H) 5.32 (t, J=4.9 Hz, 1H) 7.03 (d, J=0.76 Hz, 1H) 7.24 (d, J=9.1 Hz, 1H) 7.51 (s, 1H) 7.95 (d, J=9.6 Hz, 1H) 10.03 (br.s., 1H). $^{13}$C-NMR (100 MHz, CDCl$_3$) 9.85, 22.42, 22.53, 30.90, 35.92, 36.57, 45.01, 45.55, 52.31, 56.22, 78.25, 95.69, 112.46, 114.27, 116.77, 120.24, 121.95, 148.70, 151.49, 158.16, 160.63, 164.89, 170.36, 174.10, 178.76.

mp: 134.8° C.

[α]D: −13.8

HRMS: 485.17776-mass fits with formula $C_{25}H_{29}N_2O_6S$
Calculated mass 485.17463

Example 10

Synthesis of XIII, methyl (1R,2R,4R)-2-[[(1R,2S)-1-(ethoxycarbonyl)-2-vinylcyclopropyl]carbamoyl]-4-[[2-(4-isopropyl-1,3-thiazol-2-yl)-7-methoxy-8-methyl-4-quinolinyl]oxy]cyclopentanecarboxylate

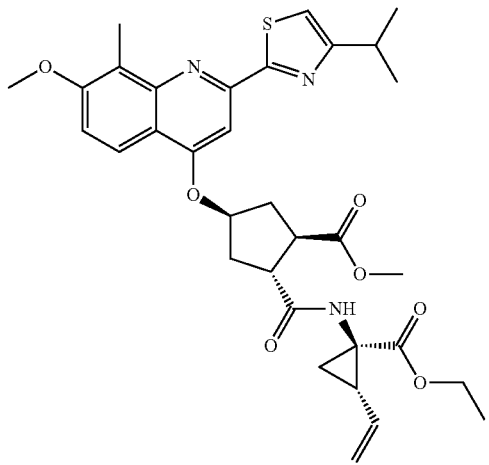 [SMILES: C=C[C@@H]1C[C@]1(NC(=O)[C@@H]1C[C@@H](Oc2cc(-c3nc(C(C)C)cs3)nc3c(C)c(OC)ccc23)C[C@H]1C(=O)OC)C(=O)OCC]

To a solution of (1R,2R,4R)-4-[[2-(4-isopropyl-1,3-thiazol-2-yl)-7-methoxy-8-methyl-4-quinolinyl]oxy]-2-(methoxycarbonyl)cyclopentanecarboxylic acid (XII, 3 g, 6.19 mmol) in THF (31 ml) was added a 1M aqueous solution of NaHCO$_3$ (6.0 ml) and the resulting solution stirred at 22° C. for 15 minutes. 2-Ethoxy-1-ethoxycarbonyl-1,2-dihydroquinoline (1.61 g, 6.50 mmol) and ethyl (1R,2S)-1-amino-2-vinylcyclopropanecarboxylate. 4-methylbenzenesulfonate (XXII.TsOH, 2.03 g, 6.19 mmol) were added and the mixture stirred at 22° C. for 16 hours. 1M aqueous HCl (12.4 ml) was added to the reaction and the mixture stirred for a few minutes. 2-Methyltetrahydrofuran (31 ml) was added to the reaction mixture and the two phases separated. The organic layer was washed with 1M aqueous NaOH (12.4 ml) and water (9.3 ml) before being dried over Na$_2$SO$_4$, filtered and the filtrate evaporated to dryness. The residue was recrystallized from isopropanol (18.6 ml) to yield after drying 2.2 g methyl (1R,2R,4R)-2-[[(1R,2S)-1-(ethoxycarbonyl)-2-vinylcyclopropyl]carbamoyl]-4-[[2-(4-isopropyl-1,3-thiazol-2-yl)-7-methoxy-8-methyl-4-quinolinyl]oxy]cyclopentanecarboxylate (XIII) as an off white solid.

$^1$H-NMR (600 MHz, CD$_2$Cl$_2$) δ ppm 1.11 (t, J=7.8 Hz, 3H) 1.29 (d, J=6.8 Hz, 6H) 1.36 (dd, J=9.44, 5.29 Hz, 1H) 1.72 (dd, J=7.93, 5.29 Hz, 1H) 2.01-2.06 (m, 1H) 2.25-2.34 (m, 2H) 2.34-2.39 (m, 1H) 2.50-2.55 (m, 1H) 2.56 (s, 3H) 3.04-3.12 (m, 1H) 3.14-3.19 (m, 1H) 3.29-3.34 (m, 1H) 3.53 (s, 3H) 3.88 (s, 3H) 3.96-4.07 (m, 2H) 5.02 (dd, J=10.39, 1.70 Hz, 1H) 5.17-5.23 (m, 2H) (m, 2H) 5.61-5.69 (m, 1H) 6.68 (s, 1H) 6.96 (d, J=0.76 Hz, 1H) 7.15 (d, J=9.06 Hz, 1H) 7.42 (s, 1H) 7.83 (d, J=9.06 Hz, 1H) $^{13}$C-NMR (150 MHz, CD$_2$Cl$_2$) 10.17 14.52 22.75 23.50 31.69 33.99 36.22 36.32 40.77 46.25 46.73 52.79 56.68 61.91 79.45 96.27 112.76 114.80 117.34 117.93 120.70 122.12 134.41 149.15 152.41 158.76 161.25 165.59 170.18 170.53 174.58 175.65.

[α]$_D$: −6.5 mp: 155.4° C.

Example 11

Synthesis of XIV, (1R,2R,4R)-2-[[(1R,2S)-1-(ethoxycarbonyl)-2-vinylcyclopropyl]carbamoyl]-4-[[2-(4-isopropyl-1,3-thiazol-2-yl)-7-methoxy-8-methyl-4-quinolinyl]oxy]cyclopentanecarboxylic acid

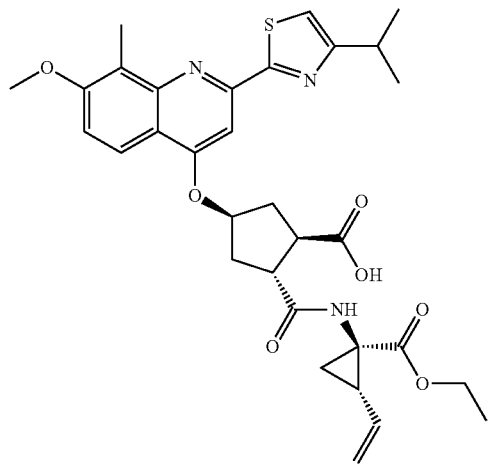 [SMILES: C=C[C@@H]1C[C@]1(NC(=O)[C@@H]1C[C@@H](Oc2cc(-c3nc(C(C)C)cs3)nc3c(C)c(OC)ccc23)C[C@H]1C(=O)O)C(=O)OCC]

To a solution of methyl (1R,2R,4R)-2-[[(1R,2S)-1-(ethoxycarbonyl)-2-vinylcyclopropyl]carbamoyl]-4-[[2-(4-isopropyl-1,3-thiazol-2-yl)-7-methoxy-8-methyl-4-quinolinyl]oxy]cyclopentanecarboxylate (XIII, 0.97 g, 1.5 mmol) in THF (6 ml) was added a solution of LiOH (66 mg, 1.57 mmol) in water (1.5 ml). The resulting mixture was stirred at 22° C. for 16 hours. Water (6 ml) and 2-methyltetrahydrofuran (10 ml) were added and the two layers separated. The aqueous phase was extracted with 2-methyltetrahydrofuran (5 ml). The combined organic layers were washed with 1N aqueous HCl (5 ml), dried over Na$_2$SO$_4$, filtered and evaporated to dryness to yield 0.74 g of (1R,2R,4R)-2-[[(1R,2S)-1-(ethoxycarbonyl)-2-vinylcyclopropyl]carbamoyl]-4-[[2-(4-isopropyl-1,3-thiazol-2-yl)-7-methoxy-8-methyl-4-quinolinyl]oxy]cyclopentanecarboxylic acid (XIV) as a yellow solid. Analysis showed this to be >90% pure and was used in the following step with no further purification.

HRMS 608.24262
Calculated mass 608.24304

Example 12

Synthesis of XV, ethyl (1R,2S)-1-([[(1R,2R,4R)-2-[hex-5-en-1-yl(methyl)-carbamoyl]-4-[[2-(4-isopropyl-1,3-thiazol-2-yl)-7-methoxy-8-methylquinolin-4-yl]-oxy]cyclopentyl]carbonyl]amino)-2-vinylcyclopropanecarboxylate

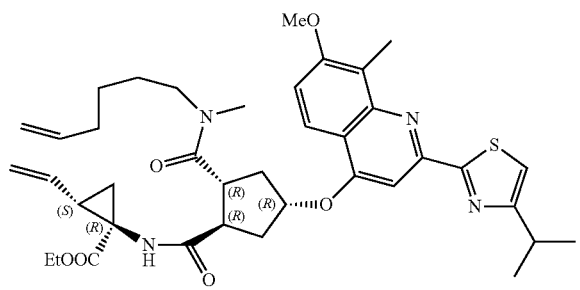

To a solution of (1R,2R,4R)-2-[[(1R,2S)-1-(ethoxycarbonyl)-2-vinylcyclopropyl]-carbamoyl]-4-[[2-(4-isopropyl-1,3-thiazol-2-yl)-7-methoxy-8-methyl-4-quinolinyl]-oxy]cyclopentanecarboxylic acid (XIV, 0.64 g, 1 mmol) and N-methyl-5-hexen-1-amine (131 mg, 1.2 mmol) in THF (10 ml) was added 1-ethoxycabonyl-2-ethoxy-1,2-dihydroquinoline (300 mg, 1.2 mmol). The resulting mixture was heated to reflux for 4 hours. The solution was allowed to cool to 22° C. and 2-methyltetrahydrofuran (10 ml) added. The organic solution was washed with 1N aqueous HCl (4.2 ml, 4.2 mmol) and water (2.1 ml) before being dried over Na$_2$SO$_4$, filtered and evaporated to dryness to yield 480 mg of ethyl (1R,2S)-1-([[(1R,2R,4R)-2-[hex-5-en-1-yl(methyl)carbamoyl]-4-[[2-(4-isopropyl-1,3-thiazol-2-yl)-7-methoxy-8-methylquinolin-4-yl]oxy]cyclopentyl]-carbonyl]amino)-2-vinylcyclopropanecarboxylate as a glassy oil LC and NMR analysis show >90% purity.

LC-MS: m/z=703 ([M+H]$^+$).

$^1$H-NMR (400 MHz, DMSO-d$_6$-mixture of rotamers) δ ppm 0.87 (t, J=7.30 Hz, 1H) 1.06-1.19 (m, 3H) 1.19-1.31 (m, 2H) 1.33 (d, J=6.80 Hz, 6H) 1.35-1.45 (m, 2H) 1.46-1.66 (m, 2H) 1.84-2.00 (m, 2H) 2.00-2.18 (m, 3H) 2.25-2.36 (m, 1H) 2.58 (s, 3H) 2.64-2.77 (m, 1H) 2.80 (s, 3H-one rotamer) 3.00 (s, 3H-one rotamer) 3.08-3.30 (m, 2H) 3.34-3.52 (m, 3H) 3.97 (s, 3H) 3.98-4.12 (m, 2H) 4.82-5.13 (m, 3H) 5.18-5.37 (m, 2H) 5.55-5.86 (m, 2H) 7.39-7.50 (m, 3H) 8.06 (t, J=8.94 Hz, 1H) 8.59 (s, 1H-one rotamer) 8.73 (s, 1H-one rotamer).

C-NMR (100 MHz, DMSO-d$_6$-mixture of rotamers) δ ppm 9.79, 13.80, 13.96, 13.99, 14.12, 14.53, 18.59, 22.21, 22.30, 25.25, 25.32, 26.02, 27.64, 30.40, 32.07, 32.14, 32.81, 33.19, 34.64, 34.68, 36.31, 36.76, 36.95, 36.98, 42.28, 46.01, 46.43, 46.74, 48.74, 56.10, 60.33, 60.51, 60.59, 78.73, 78.80, 95.34, 95.38, 112.67, 112.76, 114.67, 114.88, 115.47, 116.20, 116.23, 117.34, 120.03, 120.05, 120.59, 120.62, 134.13, 134.18, 138.41, 138.49, 147.85, 151.22, 157.98, 158.0, 160.75, 164.25, 168.66, 168.69, 169.82, 169.85, 172.48, 172.51, 173.66, 173.83

Example 13

Synthesis of XIX (R$_2$=p-NO$_2$), benzyl methyl (1R,2R,4S)-4-[(4-nitro-benzoyl)oxy]-1,2-cyclopentanedicarboxylate

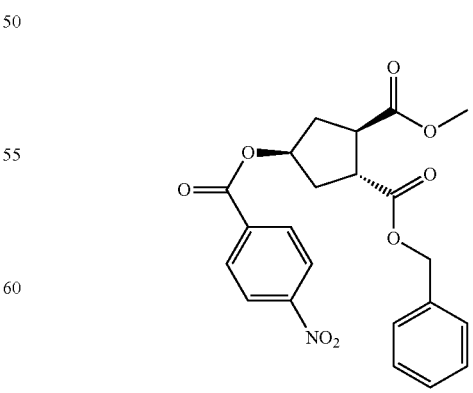

A suspension of benzyl methyl (1R,2R,4R)-4-hydroxy-1,2-cyclopentanedicarboxylate (X, 96 g, 0.34 mol), 4-nitrobenzoic acid (69.2 g, 0.41 mol) and triphenylphosphine (120.3 g, 0.46 mol) in toluene (1380 ml) was heated to reflux in a vessel equipped with a Dean-Stark trap for 30 minutes to remove all traces of water. The mixture was cooled to −5° C. and diisopropyl azodicarboxylate (92.8 g, 0.46 mol) added dropwise. The resulting mixture was stirred at 0° C. a further 60 minutes before being allowed to warm slowly to 22° C. and stirred for 12 hours. Water (345 ml) was added and the resulting mixture stirred for 10 minutes. The solids and were filtered and washed with toluene (86 ml). Distill from the filtrate 1200 ml solvent off. The mixture was cooled to 70° C. and isopropanol (1380 ml) was added. 1460 ml solvent was distilled off and the mixture cooled to 70° C. Isopropanol (690 ml) was added and the mixture heated to reflux. The mixture was allowed to cool slowly to 22° C. and stirred a further 2 hours. Filter the solids and wash with isopropanol (69 ml). Solid material was dried under vacuum to yield 80.2 g of benzyl methyl (1R,2R,4S)-4-[(4-nitrobenzoyl)oxy]-1,2-cyclopentanedicarboxylate as an off white solid.

$^1$H-NMR (400 MHz, CDCl$_3$) δ ppm 2.15-2.36 (m, 2H) 2.36-2.46 (m, 1H) 2.46-2.59 (m, 1H) 3.28-3.38 (m, 1H) 3.57-3.64 (m, 1H) 3.65 (s, 3H) 5.17 (d, J=2.5 Hz, 2H) 5.49-5.53 (m, 1H) 7.33-7.39 (m, 5H) 8.15 (d, J=9.1 Hz, 2H) 8.28 (d, J=8.8 Hz, 2H)

[α]D: −16.3
mp: 79.5° C.
HRMS 428.13632
Calculated mass 428.13454

Example 14

Removal of benzylic alcohol from crude intermediate X by oxidation Crude intermediate X, benzyl methyl (1R,2R,4R)-4-hydroxy-1,2-cyclopentanedicarboxylate, as obtained in Example 7 (3.1 g, 11.1 mmole), in benzyl alcohol (12.5 ml, 0.12 mol) was dissolved in toluene (246 ml). To this solution, 2,2'-[1,2-ethanediylbis(iminomethanediyl)]diphenol copper$^{2+}$ salt (see Velusamy, S.; Punniyamurthy, T., Eur. J. Org. Chem., 2003, 3913) (2.05 g, 6.15 mmol) and 2,2,6,6-tetramethylpiperidine-N-oxide (0.96 g, 6.15 mmol) were added. The mixture was heated to 80° C. and atmospheric air was bubbled through the solution for 3 hours. The mixture was allowed to cool to 22° C. and filtered over dicalite. The filter cake was washed with toluene. Water (246 ml) was added to the filtrate and the mixture stirred for 5 minutes. The layers were separated and to the organic phase was added water (123 ml) and sodium metabisulfite (46.76 g, 0.24 mmol). The resulting mixture was stirred at 22° C. for 10 minutes and then filtered over dicalite. The two layers of the filtrate were separated and the organic phase washed with water (123 ml) and then 2M aqueous HCl (240 ml). The organic solution was dried over Na$_2$SO$_4$, filtered and evaporated to dryness on the rotavapor to yield 2.7 g of benzyl methyl (1R,2R,4R)-4-hydroxy-1,2-cyclopentanedicarboxylate as a light brown oil that was used directly in the following reaction.

Analysis of the product showed 95% benzyl alcohol had been removed.

Note: This reaction can also be carried out by bubbling 5% oxygen in 95% nitrogen instead of atmospheric air. Whereas this makes the reaction safer it also increases the amount of time required for the reaction to reach complete conversion.

Example 15

Synthesis of XX (R$_2$=p-NO$_2$), (1R,2R,4R)-2-(methoxycarbonyl)-4-[(4-nitrobenzoyl)oxy]cyclopentanecarboxylic acid

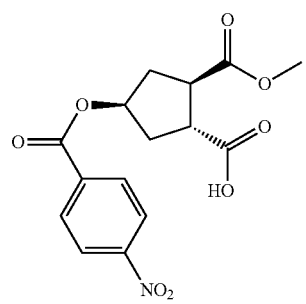 [SMILES: COC(=O)[C@@H]1C[C@H](OC(=O)c2ccc([N+](=O)[O-])cc2)C[C@H]1C(=O)O]

To a suspension of benzyl methyl (1R,2R,4S)-4-[(4-nitrobenzoyl)oxy]-1,2-cyclopentanedicarboxylate (XIX, 29 g, 67.8 mmol) and sodium formate (6.92 g, 102 mmol) in DMF (204 ml) under an atmosphere of nitrogen was added palladium (II) acetate (762 mg, 3.4 mmol). The mixture was heated to 100° C. for 3 hours. The reaction was cooled to 70° C. and filtered through Celite®. The filter cake was washed with DMF (10 ml). The combined filtrate and washings were acidified to pH 1 with HClcp and the resulting solution poured in to water (610 ml). The resulting mixture was stirred at 22° C. for 10 to 15 minutes. The solids were filtered and washed with water (14 ml) to yield after drying 18.4 g of (1R,2R,4R)-2-(methoxycarbonyl)-4-[(4-nitrobenzoyl)oxy]-cyclopentanecarboxylic acid as a red/brown solid.

$^1$H-NMR (600 MHz, CDCl$_3$) δ ppm 2.24-2.36 (m, 2H) 2.40-2.45 (m, 1H) 2.50-2.55 (m, 1H) 3.34-3.38 (m, 1H) 3.59-3.64 (m, 1H) 3.70 (s, 3H) 5.51-5.54 (m, 1H) 8.16 (d, J=9.0 Hz, 2H) 8.29 (d, J=8.9 Hz, 2H) $^{13}$C-NMR (150 MHz, CDCl$_3$) δ6.06, 36.65, 45.11, 45.11, 52.41, 77.02, 123.58, 130.77, 135.47, 150.62, 164.02, 174.40, 177.64.

[α]$_D$: −22.6
mp: 111° C.
HRMS: 338.08726
Calculated mass: 338.08759

Example 16

Synthesis of XXI (R$_2$=p-NO$_2$), (1R,3R,4R)-3-[5-hexen-1-yl(methyl)-carbamoyl]-4-(methoxycarbonyl)cyclopentyl 4-nitrobenzoate

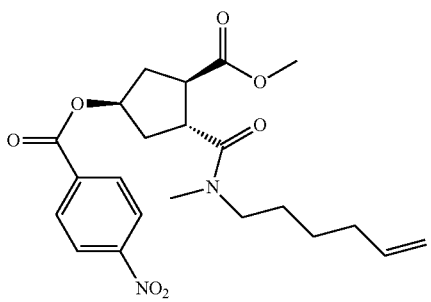 [SMILES: C=CCCCCN(C)C(=O)[C@@H]1C[C@@H](OC(=O)c2ccc([N+](=O)[O-])cc2)C[C@H]1C(=O)OC]

To a solution of (1R,2R,4R)-2-(methoxycarbonyl)-4-[(4-nitrobenzoyl)oxy]cyclopentanecarboxylic acid (XX, 15.3 g, 39.0 mmol) and N-methyl-5-hexen-1-amine (5.30 g, 46.8 mmol) in THF (78 ml) was added 1-ethoxycabonyl-2-ethoxy-1,2-dihydroquinoline (12.06 g, 48.76 mmol) and the mixture heated to 50° C. for 8 hours. The mixture was cooled to 22° C. and add 5N aqueous HCl (23.4 ml, 117.0 mmol) was added and the mixture was stirred vigorously for 2 minutes. 2-Methyltetrahydrofuran (78 ml) was added and the two layers were separated. The organic layer was washed with 1M aqueous sodium bicarbonate (57 ml) and water (29 ml) before being dried over $Na_2SO_4$, filtered and evaporated to dryness. The crude material was purified by column chromatography over silica gel eluting with heptane/ethyl acetate (1:1) to yield 11.5 g of (1R,3R,4R)-3-[5-hexen-1-yl(methyl)carbamoyl]-4-(methoxycarbonyl)-cyclopentyl 4-nitrobenzoate as a pale yellow oil.

$^1$H-NMR (600 MHz, $CDCl_3$-mixture of rotamers) δ ppm 1.24 (t, J=7.2 Hz, 2H) 1.36-1.44 (m, 2H) 1.52-1.57 (m, 1H) 1.6-1.67 (m, 1H) 2.08 (q, J=7.2 Hz, 2H) 2.17-2.24 (m, 1H) 2.27-2.32 (m, 1H) 2.54-2.61 (m, 1H) 2.96 (s, 3H-one rotamer) 3.10 (s, 3H-one rotamer) 3.41 (t, J=7.5 Hz, 1H) 3.44-3.50 (m, 1H) 3.66 (s, 3H) 3.68-3.72 (m, 1H) 3.76-3.80 (m, 1H) 4.94-5.02 (m, 2H) 5.53-5.59 (m, 1H) 5.72-5.81 (m, 1H) 8.16 (d, J=9.1 Hz, 2H) 8.29 (d, J=8.3 Hz, 2H) $^{13}$C-NMR (150 MHz, $CDCl_3$-mixture of rotamers) 25.86, 26.53, 28.13, 33.41, 34.08, 35.40, 36.22, 37.16, 37.83, 41.64, 42.17, 46.01, 48.04, 49.86, 52.18, 77.88, 114.74, 115.14, 123.59, 130.71, 135.61, 137.96, 138.48, 150.57, 164.02, 173.12, 173.38, 175.07.

HRMS: 433.19708

Calculated mass: 433.19748

Example 17

Synthesis of XVIII ($R_1$=Me), methyl (1R,2R,4R)-2-[5-hexen-1-yl-(methyl)carbamoyl]-4-hydroxycyclopentanecarboxylate

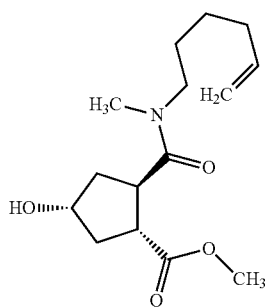 [SMILES: C=CCCCCN(C)C(=O)[C@@H]1C[C@@H](O)C[C@H]1C(=O)OC]

Sodium carbonate (980 mg, 9.25 mmol) was added to a solution of (1R,3R,4R)-3-[5-hexen-1-yl(methyl)carbamoyl]-4-(methoxycarbonyl)cyclopentyl 4-nitrobenzoate (XXI, 4.0 g, 9.25 mmol) in methanol (46 ml) and the heterogeneous mixture stirred at 22° C. for 90 minutes. The reaction mixture was filtered and the solids were washed with methanol (20 ml). The combined methanol solutions were evaporated to dryness. The residue was titrated with methanol (9 ml) and the solids filtered. The filtrate was evaporated to dryness to yield 2.7 g of a yellow oil that solidified on standing. LC analysis showed the isolated material to be a mixture of methyl (1R,2R,4R)-2-[5-hexen-1-yl(methyl)carbamoyl]-4-hydroxycyclopentanecarboxylate (52 wt/wt %) and methyl-4-nitrobenzoate. This material was used in the following step with no further purification.

Example 18

Synthesis of D, methyl (1R,2R,4S)-2-[5-hexen-1-yl(methyl)carbamoyl]-4-[[2-(4-isopropyl-1,3-thiazol-2-yl)-7-methoxy-8-methyl-4-quinolinyl]oxy]cyclopentanecarboxylate

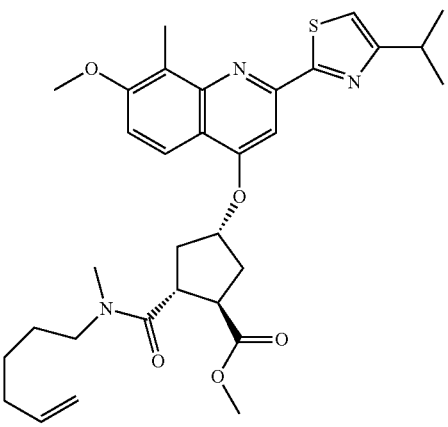 [SMILES: C=CCCCCN(C)C(=O)[C@@H]1C[C@H](Oc2cc(-c3nc(C(C)C)cs3)nc3c(C)c(OC)ccc23)C[C@H]1C(=O)OC]

2-(4-isopropyl-1,3-thiazol-2-yl)-7-methoxy-8-methyl-4(1H)-quinolinone (Quin-OH, 1.27 g, 4.0 mmole) was added to the crude solution of methyl (1R,2R,4R)-2-[5-hexen-1-yl(methyl)carbamoyl]-4-hydroxycyclopentanecarboxylate (XVIII, 2.2 g, 4.0 mmol) in toluene (28 ml). Triphenylphosphine (1.11 g, 4.25 mmol) was added and the mixture was cooled to −5° C. Diisopropyl azodicarboxylate (860 mg, 4.25 mmole) was added dropwise at such a rate that the temperature remained under 5° C. The mixture was stirred at 0° C. a further 60 minutes before being allowed to warm to 22° C. and stir for 16 hours. The reaction mixture was filtered and the solids washed with toluene. The combined toluene solution was evaporated to dryness and the residue purified by column chromatography over silica gel eluting with heptane/ethyl acetate (7:3) to yield 1.6 g of methyl (1R,2R,4S)-2-[5-hexen-1-yl(methyl)carbamoyl]-4-[[2-(4-isopropyl-1,3-thiazol-2-yl)-7-methoxy-8-methyl-4-quinolinyl]oxy]cyclopentanecarboxylate as a beige solid.

LC, MS and NMR analysis were identical to those already reported.

As used herein, the weight % (w/w %) of salts in solution always refers to the w/w % of the parent acid in the solution. For example, a 25 w/w % VI.2NMM solution (VI.2NMM referring to the (2:1) N-morpholine salt of compound VI) in a solvent refers to a solution of VI.2NMM in which 25 g of parent acid VI were present in 100 g of the solution).

Example 19

735 mg of 23.7 w/w % aqueous solution of VI, bis-potassium salt (1 mmol) was diluted in 4 ml water and mixed with 364 μL of NMM (3.3 mmol). 203 mg (1.1 mmol) TCT was added and the reaction mixture was stirred overnight at room temperature before dilution to a final volume of 10 ml to give a 63 mM aqueous solution of VII (yield: 63%).

Example 20

735 mg of 23.7 w/w % aqueous solution of VI, bis-potassium salt (1 mmol) was diluted in 4 ml water and mixed with 728 µL of NMM (6.6 mmol). 406 mg (2.2 mmol) TCT was added and the reaction mixture was stirred overnight at room temperature before dilution to a final volume of 10 ml to give a 78 mM aqueous solution of VII (yield: 78%).

Example 21

728 µL of NMM (6.6 mmol) was mixed with 4 ml water and 406 mg (2.2 mmol) TCT was added. The mixture was stirred a few minutes before adding 735 mg of 23.7 w/w % aqueous solution of VI, bis-potassium salt (1 mmol). The resulting reaction mixture was further stirred overnight at room temperature before dilution to a final volume of 10 ml to give a 57 mM aqueous solution of VII (yield: 57%).

Example 22

735 mg of 23.7 w/w % aqueous solution of VI, bis-potassium salt (1 mmol) was diluted in 4 ml water and mixed with 221 µL NMM (2 mmol). 648 mg (2.2 mmol) DMTMM.H$_2$O was added and the reaction mixture was stirred overnight at room temperature before dilution to a final volume of 10 ml to give a 54 mM aqueous solution of VII (yield: 54%).

Example 23

386 mg (2.2 mmol) CDMT was dissolved in 4 ml acetone and 463 µL (4.2 mmol) NMMR was added. The mixture was stirred a few minutes then 735 mg of 23.7 w/w % aqueous solution of VI, bis-potassium salt was added. The resulting mixture was further stirred overnight at room temperature before dilution to a final volume of 10 ml to give a 69 mM solution of VII (yield: 69%).

Example 24

386 mg (2.2 mmol) CDMT was dissolved in 4 ml MeTHF and 463 µL (4.2 mmol) NMM was added. The mixture was stirred a few minutes then 735 mg of 23.7 w/w % aqueous solution of VI, bis-potassium salt was added. The resulting mixture was further stirred overnight at room temperature before dilution to a final volume of 10 ml to give a 54 mM solution of VII (yield: 54%).

Example 25

5.66 g (32.2 mmol) CDMT was dissolved in 59 ml MeTHF. 3.7 ml (33.7 mmol) NMM was added and the mixture was stirred 1 h at 25° C. 10.0 g of 25.5 w/w % aqueous solution of VI.2NMM (14.6 mmol) was added and the resulting mixture was further stirred a few hours at 25° C. 15 ml water and 3 ml concentrated HCl were added. The mixture was stirred a few minutes, the insoluble materials were filtered off, the filtrate was decanted and the water layer was extracted with 15 ml MeTHF. The organic layers were combined and washed with 7 ml brine to give 53.1 g of 2.59 w/w % solution of VII in MeTHF, which also contained 0.23 w/w % VI (yield: 60%).

Example 26

5.66 g (32.2 mmol) CDMT was dissolved in 59 ml isopropyl acetate. 3.7 ml (33.7 mmol) NMM was added and the mixture was stirred 1 h at 25° C. 10.0 g of 25.5 w/w % aqueous solution of bis N-methylmorpholine salt of VI (14.6 mmol) was added and the resulting mixture was further stirred a few hours at 25° C. 15 ml water and 3 ml concentrated HCl were added. The mixture was stirred a few minutes, the insoluble materials were filtered off, the filtrate was decanted and the water layer was extracted with 15 ml isopropyl acetate. The organic layers were combined and washed with 7 ml brine to give 56.6 g of 1.3 w/w % solution of VII in isopropyl acetate that also contained 0.18 w/w % VI (yield: 32%).

Example 27

5.66 g (32.2 mmol) CDMT was dissolved in 59 ml acetone. 3.7 ml (33.7 mmol) NMM was added and the mixture was stirred 1 h at 25° C. 10.0 g of 25.5 w/w % aqueous solution of bis N-methylmorpholine salt of VI (14.6 mmol) was added and the resulting mixture was further stirred a few hours at 25° C. The insoluble materials were filtered off, 1 ml concentrated HCl was added to the filtrate and the filtrate was decanted. The organic layer was washed with 7 ml brine to give 44.4 g of 1.44 w/w % solution of VII in MeTHF, which also contained 0.04 w/w % VI (yield: 28%).

Example 28

19.80 g (113 mmol) CDMT was dissolved in 205 ml MeTHF. 13 ml (118 mmol) NMM was added and the mixture was stirred at 25° C. for 2 h. 35 g of 25.5 w/w % aqueous solution of bis N-methylmorpholine salt of VI (51.3 mmol) was added and the reaction mixture was stirred overnight at 25° C. 51 ml water and 10.6 ml concentrated HCl were added and the mixture was stirred a few minutes at 25° C. The resulting solid was filtered off and the filtrate was decanted. The organic layer was washed with 51 ml water and 26 ml brine to give 181.7 g of 2.13 w/w % VII solution in MeTHF (yield: 48%).

Example 29

19.80 g (113 mmol) CDMT was dissolved in 205 ml MeTHF. 13 ml (118 mmol) NMM was added and the mixture was stirred at 25° C. for 2 h. 35 g of 25.5 w/w % aqueous solution of bis N-methylmorpholine salt of VI (51.3 mmol) was mixed with 14.3 ml (102.5 mmol) triethylamine then added to the mixture of CDMT and bis N-methylmorpholine salt of VI (NMM) and the reaction mixture was stirred overnight at 25° C. 51 ml water and 19.9 ml concentrated HCl were added and the mixture was stirred a few minutes at 25° C. The resulting solid was filtered off and the filtrate was decanted. The organic layer was washed with 51 ml water and 26 ml brine to give 163.6 g of 2.56 w/w % VII solution in MeTHF (yield: 52%).

Example 30

2.83 g (16 mmol) CDMT was dissolved in 29 ml MeTHF. 1.9 ml (18 mmol) NMM was added and the mixture was stirred at 20° C. for 1 h. 52.01 g of 2.59 w/w % solution of VII in MeTHF (8.7 mmol) [from Example 25] was mixed with 1.82 g NMHA and 232 µL (2.9 mmol) NMM and the resulting solution was added to the mixture of CDMT-NMM in MeTHF. The reaction mixture was stirred overnight at 20° C. 14.6 ml water and 1 ml concentrated HCl were added. The mixture was decanted and the organic layer was successively washed with 14.6 ml water, 14.6 ml water containing 150 mg NaOH and 7.3 ml water, then dried over magnesium sulfate. The insoluble materials were filtered off to give 83.1 g of 2.51 w/w % solution of XVII in MeTHF (yield: 96%-57% from bis N-methylmorpholine salt of VI).

Example 31

2.83 g (16 mmol) CDMT was dissolved in 29 ml isopropyl acetate. 1.9 ml (18 mmol) NMM was added and the mixture was stirred at 20° C. for 1 h. 55.5 g of 1.3 w/w % solution of VII in isopropyl acetate (4.7 mmol) [from Example 26] was mixed with 1.82 g N-methyl-5-hexen-1-amine (NMHA) and 232 µL (2.9 mmol) NMM and the resulting solution was added to the mixture of CDMT-NMM in isopropyl acetate. The reaction mixture was stirred overnight at 20° C. 14.6 ml water and 1 ml concentrated HCl were added. The mixture was decanted and the organic layer was successively washed with 14.6 ml water, 14.6 ml water containing 150 mg NaOH and 7.3 ml water then dried over magnesium sulfate. The insoluble materials were filtered off to give 82.51 g of 1.43 w/w % solution of XVII in isopropyl acetate (yield: quantitative—33% from bis N-methylmorpholine salt of VI).

Example 32

2.83 g (16 mmol) CDMT was dissolved in 29 ml acetone. 1.9 ml (18 mmol) NMM was added and the mixture was stirred at 20° C. for 1 h. 43.3 g of 1.44 w/w % solution of VII in acetone (4.7 mmol) [from Example 27] was mixed with 1.82 g NMHA and 232 µL (2.9 mmol) NMM and the resulting solution was added to the mixture of CDMT-NMM in acetone. The reaction mixture was stirred overnight at 20° C. Acetone was removed under vacuum and the residues was partitioned in toluene (59 ml)—water (14.6 ml)—concentrated HCl (1 ml) mixture. The layers were separated and the organic layer was successively washed with 14.6 ml water, 14.6 ml water containing 150 mg NaOH and 7.3 ml water then dried over magnesium sulfate. The insoluble materials were filtered off to give 74.27 g of 1.41 w/w % solution of XVII in toluene (yield: quantitative-29% from bis N-methylmorpholine salt of VI).

Example 33

9.90 g (56.4 mmol) CDMT was dissolved in 103 ml MeTHF. 6.8 ml (61.5 mmol) NMM was added and the mixture was stirred at 25° C. for 2 h. 162.2 g 2.13 w/w % solution of VII in MeTHF [from Example 28] was mixed with 0.71 ml (5.1 mmol) triethylamine and 6.38 g (56.4 mmol) NMHA then added to the mixture of CDMT-NMM. The reaction mixture was stirred for 3 h at 25° C. 51 ml water and 3 ml concentrated HCl were added and the mixture was stirred for a few minutes. The resulting solid was filtered off and the filtrate was decanted. The organic layer was successively washed with 26 ml water, 51 ml water containing 0.6 g NaOH and 26 ml water, then dried over magnesium sulfate. The insoluble materials were filtered off to give 265.4 g of 2.51 w/w % solution of XVII in MeTHF (yield: quant-54% from bis N-methylmorpholine salt of VI).

Example 34

9.90 g (56.4 mmol) CDMT was dissolved in 103 ml MeTHF. 6.8 ml (61.5 mmol) NMM was added and the mixture was stirred at 25° C. for 2 h. 180.2 g 2.56 w/w % solution of VII in MeTHF [from Example 29] was mixed with 0.71 ml (5.1 mmol) triethylamine and 6.38 g (56.4 mmol) NMHA then added to the mixture of CDMT-NMM. The reaction mixture was stirred 3 h at 25° C. 51 ml water and 3 ml concentrated HCl were added and the mixture was stirred a few minutes. The resulting solid was filtered off and the filtrate was decanted. The organic layer was successively washed with 26 ml water, 51 ml water containing 0.6 g NaOH and 26 ml water then dried over magnesium sulfate. The insoluble materials were filtered off to give 255.4 g of 2.91 w/w % solution of XVII in MeTHF (yield: quant-58% from bis N-methylmorpholine salt of VI).

Example 35

To 82.1 g of 2.51 w/w % solution of XVII in MeTHF [from Example 30], were added 14.6 ml methanol and 76 µL methanesulfonic acid. The solution was refluxed overnight. 125 mg sodium carbonate was added and the mixture was refluxed for an additional one hour. 51 ml solvent were distilled off (removal of methanol) and the concentrate was successively washed with 7.3 ml water and with 3.5 ml brine, dried over magnesium sulfate and filtered to give 31.1 g of 5.3 w/w % XVIII (R1=Me) solution in MeTHF (yield: 71%-41% from bis N-methylmorpholine salt of VI).

Example 36

81.4 g of 1.43 w/w % solution of XVII in isopropyl acetate [from Example 31] were concentrated under vacuum and the residue was redissolved in 59 ml toluene. 14.6 ml methanol and 76 µL methanesulfonic acid were added and the solution was refluxed overnight. 125 mg sodium carbonate was added and the mixture was refluxed 1 h more. 38 ml solvent were distilled off (removal of methanol) and the concentrate was successively washed with 7.3 ml water and with 3.5 ml brine, dried over magnesium sulfate and filtered to give 28.9 g of 3.9 w/w % XVIII (R1=Me) solution in toluene (yield: 86%-28% from bis N-methylmorpholine salt of VI).

Example 37

85.4 g of 1.45 w/w % solution of XVII in methyl isopropylketone (MIK) [from Example 31] were concentrated under vacuum and the residue was redissolved in 59 ml toluene. 14.6 ml methanol and 76 µL methanesulfonic acid were added and the solution was refluxed overnight. 125 mg sodium carbonate was added and the mixture was refluxed 1 h more. 28 ml solvent were distilled off (removal of methanol) and the concentrate was successively washed with 7.3 ml water and with 3.5 ml brine, dried over magnesium sulfate and filtered to give 38.0 g of 3.2 w/w % XVIII (R1=Me) solution in toluene (yield: 86%-30% from bis N-methylmorpholine salt of VI).

Example 38

To 73 g of 1.41 w/w % solution of XVII in toluene [from Example 32], were added 14.6 ml methanol and 76 µL methanesulfonic acid. The solution was refluxed overnight. 125 mg sodium carbonate was added and the mixture was refluxed for an additional one hour. 31 ml solvent were distilled off (removal of methanol) and the concentrate was successively washed with 7.3 ml water and with 3.5 ml brine, dried over magnesium sulfate and filtered to give 63.0 g of 1.75 w/w % XVIII (R1=Me) solution in toluene (yield: 95%-28% from bis N-methylmorpholine salt of VI).

Example 39

To 135 g of 2.51 w/w % solution of XVII in MeTHF [from Example 33], were added 26 ml methanol and 84 μL methanesulfonic acid. The solution was refluxed overnight. 136 mg sodium carbonate was added and the mixture was refluxed for one additional hour. About 52 ml solvent were distilled off (removal of methanol) and the concentrate was washed with 26 ml water, dried over magnesium sulfate and filtered to give 55.16 g of 5.30 w/w % XVIII (R1=Me) solution in MeTHF (yield: 76%-41% from bis N-methylmorpholine salt of VI).

Example 40

To 135 g of 2.51 w/w % solution of XVII in MeTHF [from Example 33], were added 154 ml toluene. 32 ml solvent were distilled off and the concentrate was cooled down to 60° C. 26 ml methanol and 84 μL methanesulfonic acid were added and the solution was refluxed overnight. 136 mg sodium carbonate was added and the mixture was refluxed 1 h more. About 52 ml solvent were distilled off (removal of methanol) and the concentrate was washed with 26 ml water, dried over magnesium sulfate and filtered to give 88.74 g of 5.21 w/w % XVIII (R1=Me) solution in MeTHF (yield: quant-65% from bis N-methylmorpholine salt of VI).

Example 41

To 126 g of 2.91 w/w % solution of XVII in MeTHF [from Example 34], were added 154 ml toluene. 190 ml solvent were distilled off and the concentrate was cooled down to 60° C. 26 ml methanol and 84 μL methanesulfonic acid were added and the solution was refluxed overnight. 136 mg sodium carbonate was added and the mixture was refluxed 1 h more. 20 ml solvent were distilled off (removal of methanol) and the concentrate was washed with 26 ml water, dried over magnesium sulfate and filtered to give 92.6 g of 2.20 w/w % XVIII (R1=Me) solution in MeTHF (yield: 49%-29% from bis N-methylmorpholine salt of VI).

The invention claimed is:
1. A process for preparing the lactone VII comprising
   (a) reacting 4-oxo-1,2-cyclopentanedicarboxylic acid (V) with brucine or (1R,2S)-(−)-ephedrine, thus preparing the bis-brucine or bis-(1R,2S)-(−)-ephedrine salt of (V), and
   (b) precipitating selectively the bis-brucine or bis-(1R,2S)-(−)-ephedrine salt of (1R,2R)-4-oxo-1,2-cyclopentanedicarboxylic acid II, while the bis-brucine or bis-(1R,2S)-(−)-ephedrine salt of [(1S,2S)-4-oxo-1,2-cyclopentanedicarboxylic acid stays in solution;
   (c) liberating the acid II by removal of brucine or (1R,2S)-(−)-ephedrine from the precipitated salt obtained in step (b);
as outlined in the following reaction scheme:

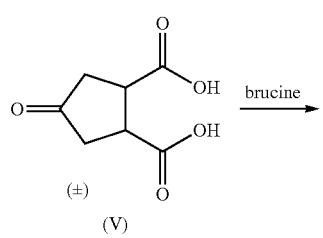

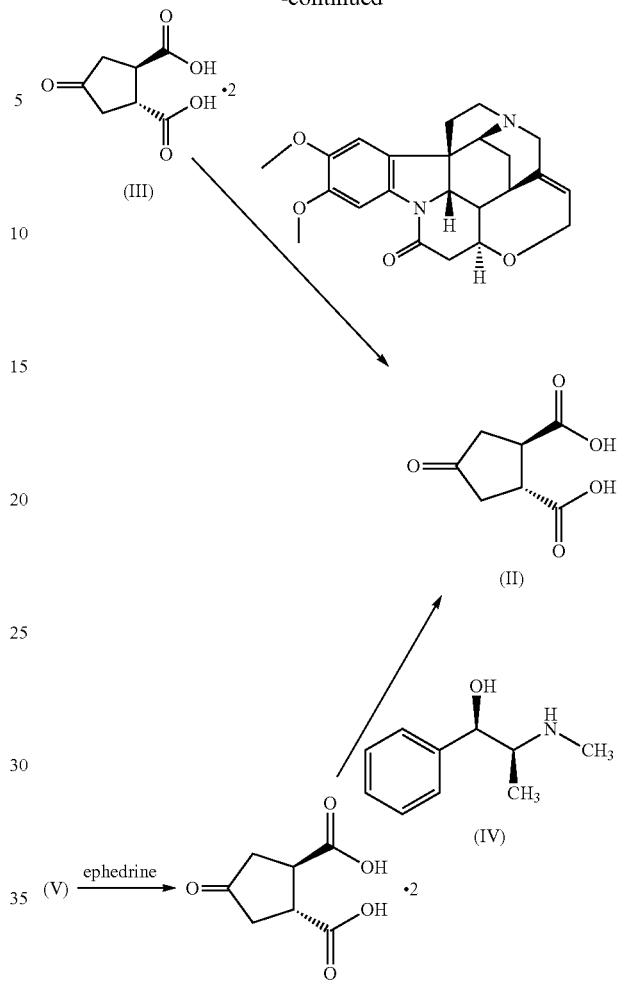

(d) reducing 4-ketocyclopentanedicarboxylic acid II, or a salt thereof, to 4-hydroxy-1,2-cyclopentanedicarboxylic acid (VI), which is cyclized to the lactone (VII), in water, and conducting the cyclization of the intermediate VI to VII without isolation of VI or removing water, with or without adding an organic solvent, using a triazine derivative, as outlined in the following reaction scheme:

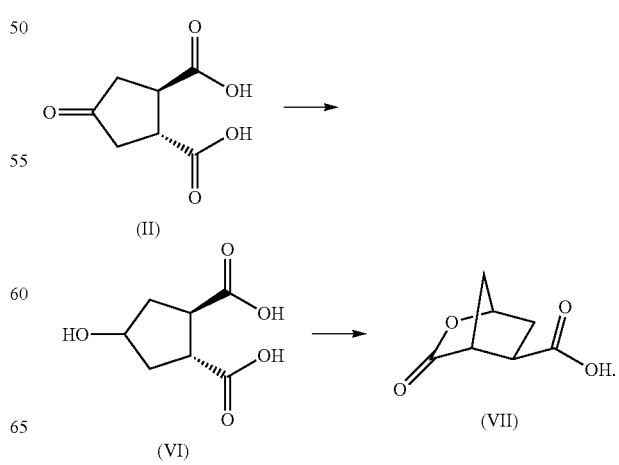

2. The process of claim 1 wherein an organic solvent is used in step (d) and the organic solvent is selected from the group consisting of acetone, methylethylketone (MEK), tetrahydrofuran (THF), MeTHF, CPME (cyclopentyl methyl ether), $C_{1-4}$alkyl acetate, $C_{1-4}$alkyl propionate, $C_{1-4}$alkyl butyrate or toluene, and the triazine is 2,4,6-trichloro-1,3,5-triazine (TCT), chloro-dimethoxytriazine (CDMT), dichloromethoxytriazine (DCMT), and N-(3,5-dimethoxytriazinyl)-N-methylmorpholinium chloride (DMTMM).

* * * * *